(12) United States Patent
Sargent et al.

(10) Patent No.: US 6,586,949 B1
(45) Date of Patent: Jul. 1, 2003

(54) VOLUME CHARGE DENSITY MEASURING SYSTEM

(76) Inventors: John S. Sargent, 1712 Manchester Pl., Escondido, CA (US) 92027; Frank T. Sargent, 9433 Brandy Cir., Fort Myers, FL (US) 33919

( * ) Notice: Subject to any disclaimer, the term of this patent is extended or adjusted under 35 U.S.C. 154(b) by 0 days.

(21) Appl. No.: 09/554,785
(22) PCT Filed: Dec. 3, 1999
(86) PCT No.: PCT/US99/28693
§ 371 (c)(1), (2), (4) Date: May 19, 2000
(87) PCT Pub. No.: WO00/34767
PCT Pub. Date: Jun. 15, 2000

(51) Int. Cl.$^7$ ............................................. G01R 27/26
(52) U.S. Cl. ......................... 324/690; 324/686; 324/664
(58) Field of Search .................. 324/686, 663, 324/688, 452, 672, 661, 30 R, 725, 71.1, 664, 689; 340/684; 73/304 C

(56) References Cited

U.S. PATENT DOCUMENTS

| | | | | |
|---|---|---|---|---|
| 3,988,668 A | | 10/1976 | Bowers | |
| 4,051,721 A | * | 10/1977 | Williams | 324/661 |
| 4,074,184 A | * | 2/1978 | Dechene et al. | 324/30 R |
| 4,112,744 A | | 9/1978 | Tassano | |
| 4,249,131 A | * | 2/1981 | Owen | 324/452 |
| 4,434,657 A | * | 3/1984 | Matsumura et al. | 73/304 C |
| 4,710,757 A | * | 12/1987 | Haase | 340/684 |
| 4,961,147 A | * | 10/1990 | Moore | 324/71.1 |
| 4,971,015 A | | 11/1990 | Gonze | |
| 4,994,749 A | * | 2/1991 | Davies et al. | 324/71.1 |
| 5,005,402 A | * | 4/1991 | Pischinger et al. | 324/663 |
| 5,027,076 A | * | 6/1991 | Horsley et al. | 324/663 |
| 5,099,386 A | * | 3/1992 | Stokes et al. | 324/725 |
| 5,151,660 A | * | 9/1992 | Powers et al. | 324/663 |
| 5,182,523 A | | 1/1993 | Ertel et al. | |
| 5,262,732 A | * | 11/1993 | Dickert et al. | 324/672 |
| 5,361,035 A | * | 11/1994 | Meitzler et al. | 324/663 |
| 5,392,657 A | * | 2/1995 | Feller | 73/861.77 |
| 5,477,727 A | * | 12/1995 | Koga | 73/304 C |
| 5,546,005 A | | 8/1996 | Rauchwerger | |
| 5,611,240 A | * | 3/1997 | Yamaguchi | 324/663 |
| 5,612,622 A | * | 3/1997 | Goldman et al. | 324/676 |
| 5,945,831 A | * | 8/1999 | Sargent et al. | 324/663 |

FOREIGN PATENT DOCUMENTS

EP  0 341 675  11/1989

* cited by examiner

Primary Examiner—Kamand Cuneo
Assistant Examiner—Jermele Hollington
(74) Attorney, Agent, or Firm—Brown, Martin, Haller & McClain, LLP

(57) ABSTRACT

A capacitive sensor includes one or more chambers through which a material can flow. Two conductors are located to partially surround the flow chamber so that the material flows between the conductors. Where more than one chamber is used, additional conductors are provided. A measurement circuit connected to the conductors provides an output corresponding to a difference between test and reference frequencies. A display indicates the measured capacitance as a continuous-scale, proportional representation or a binary representation. The sensor system can measure volume charge density of a fluid or parameters responsive to changes in volume charge density, such as flow velocity.

20 Claims, 24 Drawing Sheets

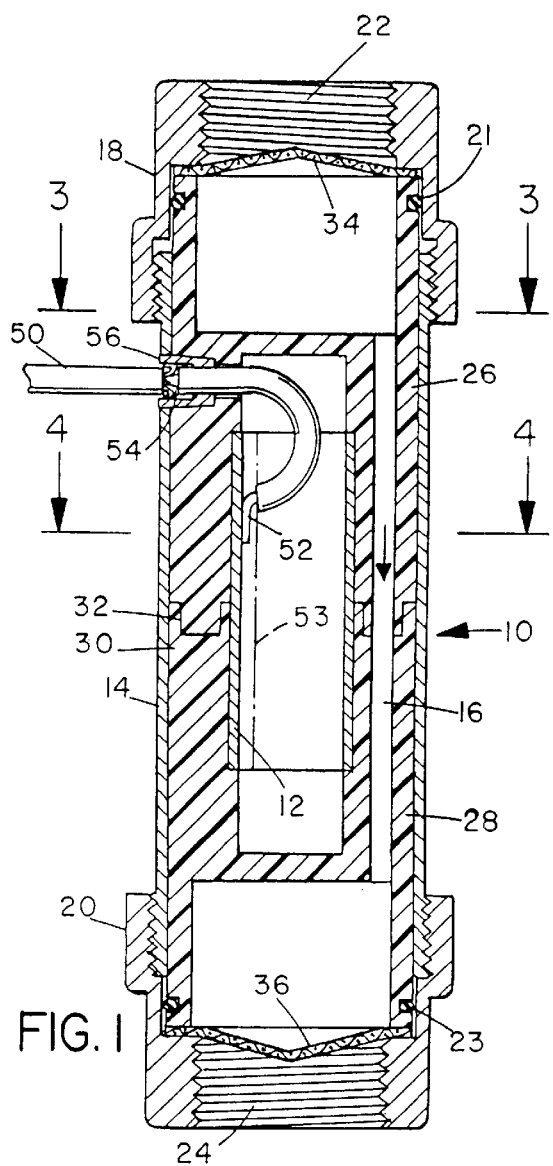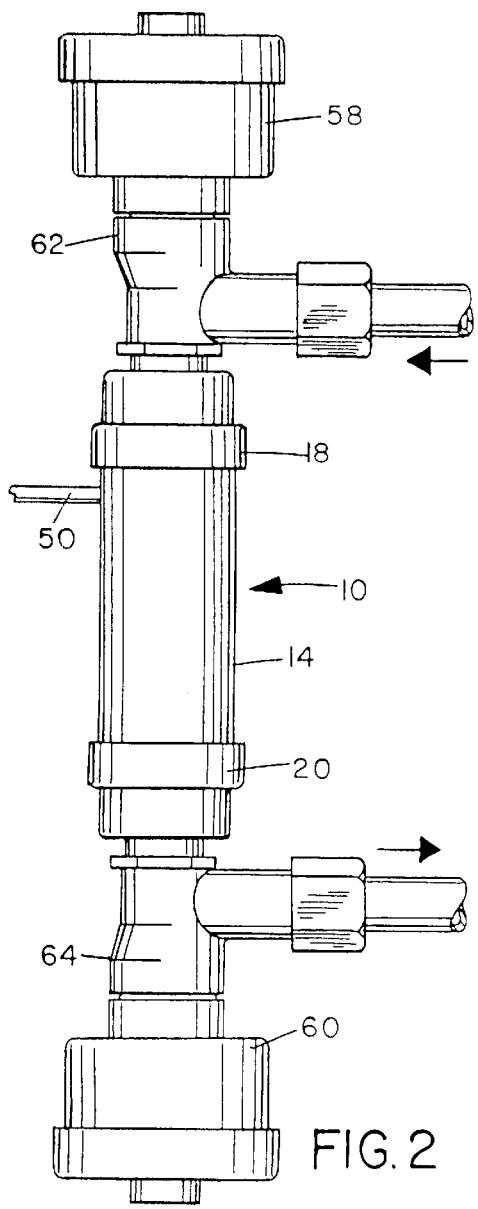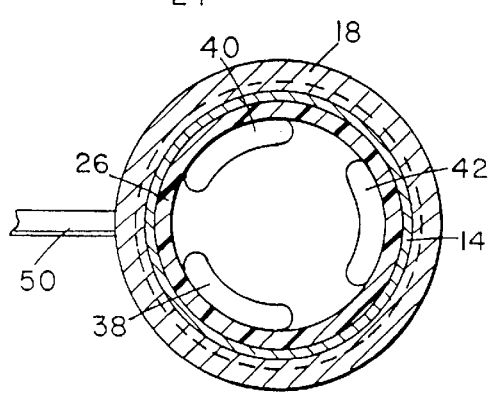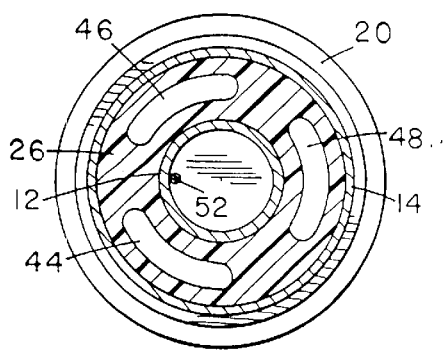

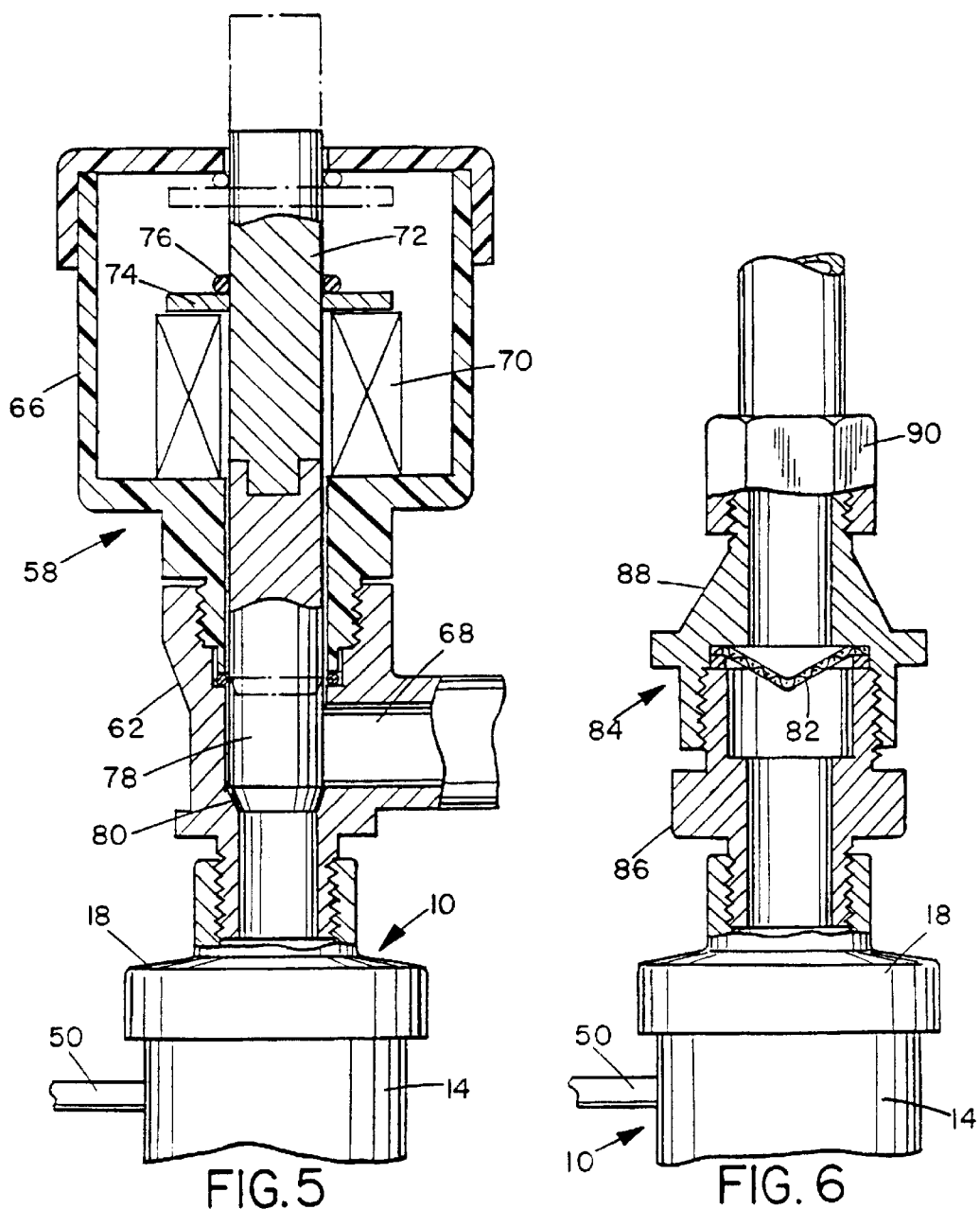

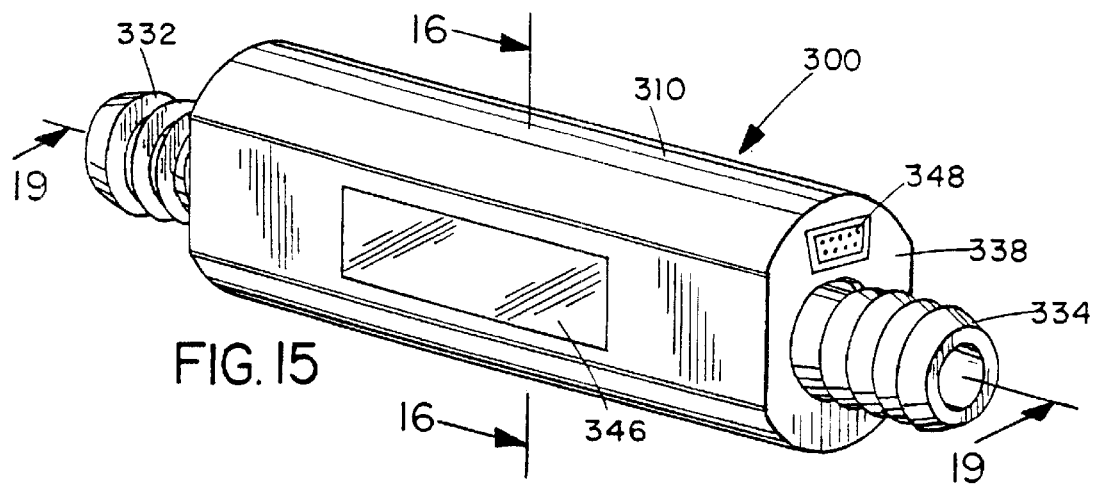
FIG. 15
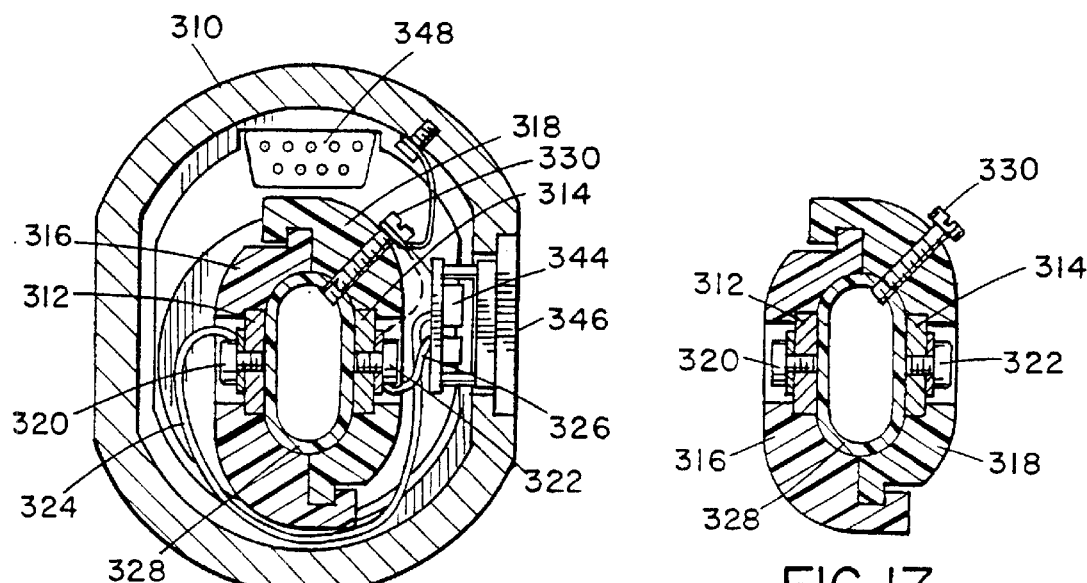
FIG. 16
FIG. 17
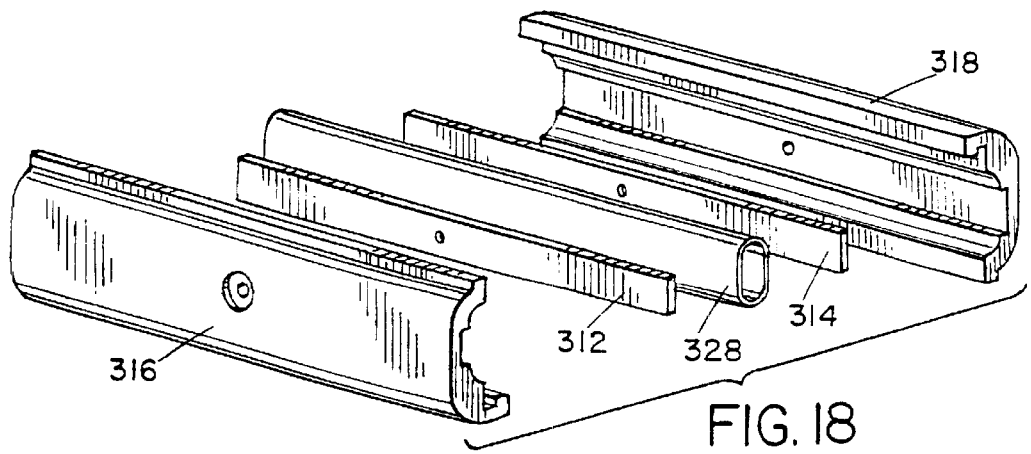
FIG. 18

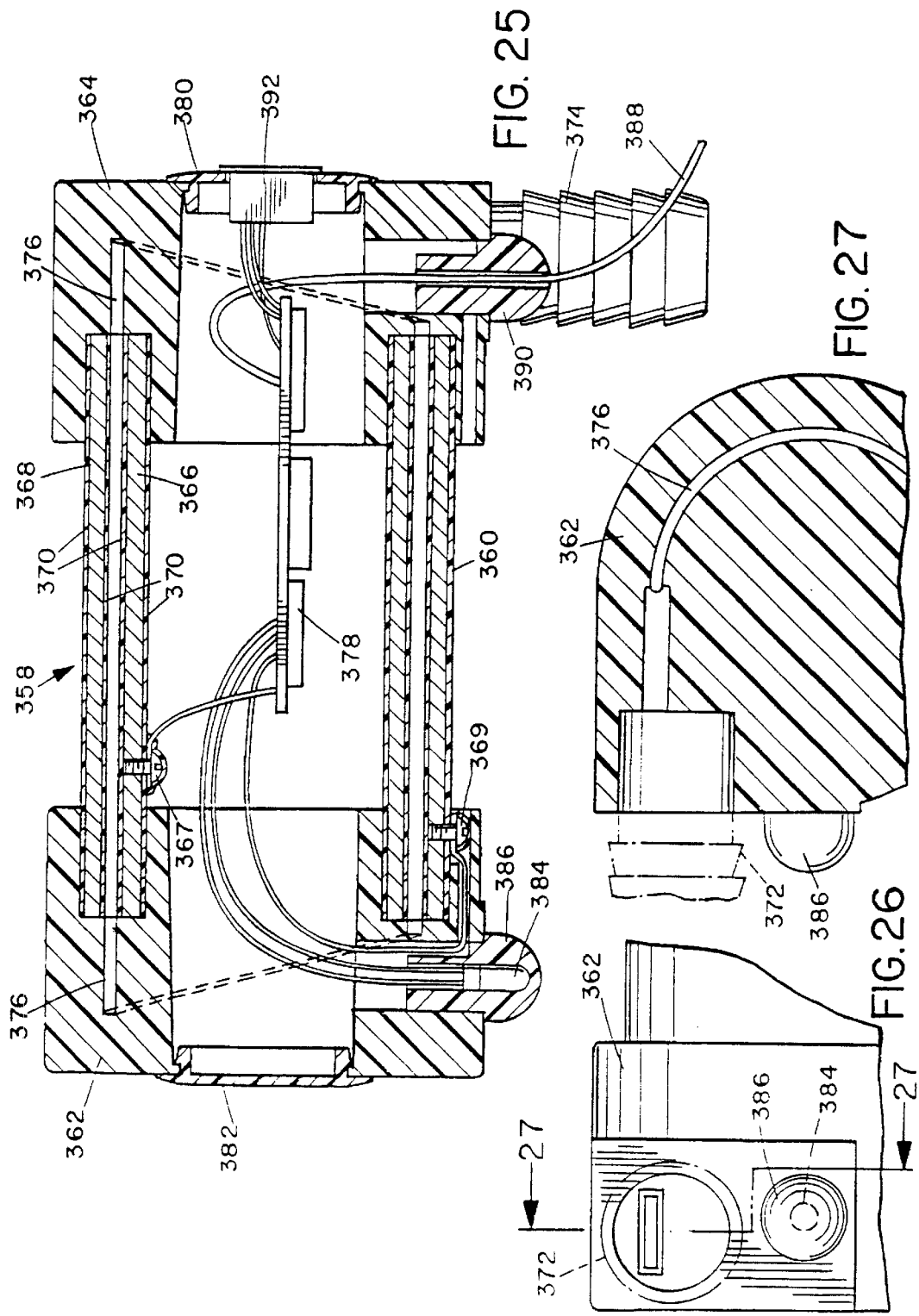

VOLUME CHARGE DENSITY MEASURING SYSTEM

RELATED APPLICATIONS

This application, filed under 35 U.S.C. 371, is a national stage filing of PCT/US99/28693 filed Dec. 3, 1999.

BACKGROUND OF THE INVENTION

1. Field of the Invention

The present invention relates generally to capacitive measuring systems and, more specifically, to systems having a sensor shielded against the detrimental effects of external electric fields and circuits for capacitively measuring the volume charge density of a sample of material.

2. Description of the Related Art

Capacitive measuring systems have been used to measure dissolved solids and impurities in fluids such as water and oil. A capacitive sensor is a device having two electrically conductive electrodes and a non-conductive body that insulates the fluid from the electrodes. The electrodes are typically tubular in shape and concentric with one another. When a sample is placed in the body, the device defines a capacitance in response to the dielectric constant of the sample. The dielectric constant varies in response to the ion concentration in the sample, which, in turn, is related to the solid impurities. The capacitance can be measured by connecting a suitable oscillator and measuring circuit to the plates. Comparing the measured capacitance to a known capacitance provides information relating to the electrical properties of the sample. For example, the dissolved solids in a sample of water can be determined by comparing the measured value to that which is produced in response to a known pure (e.g., double-distilled) sample of water.

Conventional capacitive sensors of the type described above are of low precision. They cannot, for example, consistently measure ion concentrations in water below a few parts per million. Practitioners in the art have discovered that measurements may vary over a wide range under seemingly identical test conditions. Furthermore, many of these devices are limited in their ability to handle flows of material at high pressures, and are subject to the build-up of static electricity from the flowing material, the discharge of which can interfere with accurate measurement. It would be desirable to provide a capacitive measuring system having a high-precision sensor. This and other problems and deficiencies are clearly felt in the art and are solved by the present invention in the manner described below.

SUMMARY OF THE INVENTION

The present invention includes a capacitive sensor and an electronic measurement system. In a first exemplary embodiment, the sensor includes a tubular outer conductor, a tubular inner conductor coaxial with the outer conductor, and an electrically insulated chamber between the inner and outer conductors. The material sample to be measured is placed in the chamber or forced to flow through the chamber. The chamber electrically isolates the sample from the conductors. When the sample is introduced into the chamber, it defines the dielectric of a capacitor. The plates of the capacitor are defined by the inner and outer conductors.

In a second exemplary embodiment, the sensor comprises one or more generally tubular channels or chambers through which the sample flows. Parallel conductor plates are located on each side of the channels, so that the sample flows between the conductors. Where two channels are used, three conductive plates are provided so that each channel is positioned between a pair of plates.

It has been discovered in accordance with the present invention that measurements produced by capacitive sensors known in the art are detrimentally affected by external electric fields, i.e., fields produced by environmental sources external to the sensor, such as fluorescent lights. A conductor exposed to an electric field acts as an antenna and develops a potential. If measurements are taken using such a sensor in, for example, a room having fluorescent lighting, the measurements will be markedly different than if taken in a room not having fluorescent lighting. Even in the absence of fluorescent lighting and other apparent sources of electric fields, the body of the person taking the measurements may emit sufficient electromagnetic radiation to affect the measurements.

To reduce the detrimental effect from electric fields, the present invention can include electrostatic shielding that completely encloses the chamber in which the sample is contained during measurement. In an exemplary embodiment, the sensor has one or more openings, and a removable cap made of a conductive material is attachable the opening. No external electric field can penetrate into the chamber because the cap is in electrical contact with the outer conductor and seals the opening during measurement. The electrostatic shielding can be incorporated into a housing, which can be a generally rectangular body formed from an insulating material that is coated with a conductive material. In another exemplary embodiment, the sensor has one or more openings, and a valve selectably opens or closes the opening. No external electric field can penetrate into the chamber because the valve, which may be solenoid-operated, has a conductive member that is in electrical contact with the outer conductor and seals the opening during measurement. In yet another exemplary embodiment, the sensor has one or more openings in which a screen made of a conductive material is disposed. An external electric field cannot penetrate into the chamber to any significant extent because the screen is in electrical contact with the outer conductor.

In addition to providing electrostatic shielding and general physical protection, the housing for the sensor can provide means for stabilizing the relative positions of the sensor components. In an exemplary embodiment, the housing can include a ribbed insert which supports and surrounds the tubular flow channels and the parallel plate conductors. The ribs of the insert extend along a plane orthogonal to the axes of the flow channels, resisting expansion of the channels under temperature or pressure stresses and maintaining a constant distance between the conductors and the flow channels. Additional stability can be provided by filling the ribbed insert with an epoxy material after attachment of the flow channel and conductor plate assembly. Once set, the epoxy provides significantly increased pressure tolerance, so that the sensor can be used in high pressure and/or high flow rate conditions. The epoxy can be selected to provide improved thermal insulation. The ribbed insert provides additional stabilization by minimizing shrinkage of the epoxy as itsets. In an alternative assembly procedure, the epoxy can be injected through a port in the housing after all components have been assembled, thus sealing all components to provide stability and improved protection against intrusion of dirt and moisture.

Another source of potential electrical noise that can detrimentally affect the measurement is static electricity generated by the rapid flow of material through the pipeline. This can particularly be a problem where the material contains conductive materials, such that the material has a low overall impedance. This static electricity can discharge in the sensors, resulting in spurious signals, inaccurate measurements, and can even damage the sensor's electronics. The sensor can be fitted with one or more static discharge conductors, each comprising a conductive button or extension which extends into the flow channel. In the preferred embodiment, one button is positioned at each inlet and outlet of the sensor. A wire connected to each button is grounded at its second end, typically via a ground connection on the sensor's circuit board, allowing the static to be harmlessly discharged. The button material should be inert and non-reactive relative to the material being measured since it will be in direct contact with the material. Appropriate materials can include coatings of metals such as gold, nickel or platinum.

The electronic measurement system determines the difference between a reference signal or a value representing such a signal having a constant reference frequency and a test signal or value representing such a signal having a test frequency responsive to the sensor capacitance. In an exemplary embodiment, the circuit includes D-type flip-flops that, in effect, subtract one signal from the other. In another exemplary embodiment, the circuit includes a phase-locked loop. The circuit may also include analog or digital means for improving response linearity, such as a logarithmic amplifier, look-up table, or polynomial correction. Also, the electronic measurement system may, in certain embodiments, periodically reverse the polarity of the test signal applied to the sensor in order to minimize charging of non-conductive surfaces, which promotes measurement accuracy and provides a cleaning effect and other benefits.

Temperature-compensation circuitry can be included to minimize drift in measurements arising from environmental and material temperature variations. The actual compensation is performed by the sensor microprocessor or other controller. The material temperature can be measured by conducting the temperature to a thermistor or other appropriate temperature measuring device. In an exemplary embodiment, a thermistor is integrated into the button used for static discharge, taking advantage of the thermal conductivity of the electrically-conductive coating of the button. The button is formed with a cavity in which the thermistor is sealed in place using a thermally-conductive epoxy or other thermally-conductive material. Above the thermally-conductive epoxy, between the button and the circuitry to which it attaches to the sensor's circuit board, is a thermally-insulating epoxy or other seal which prevent the transfer of heat along any pathway but the thermistor's wires. A single thermistor should provide the necessary data and can be included in either the inlet or outlet ports. However, multiple thermistors can be utilized, with one installed at each of any combination of ports if desired.

The system may be used for a variety of purposes, including measuring the extent of impurities in fluids, such as gases and water and other liquids, and measuring the flow rate of such fluids. Application of such a system can range from, for example, a purified water handling system in an integrated circuit manufacturing facility to desalination plants to oil or gas pipeline monitoring. In addition to the sensors, other components of the measurement system include communications interface modules and display devices, controllers and system software.

The foregoing, together with other features and advantages of the present invention, will become more apparent when referring to the following specification, claims, and accompanying drawings.

BRIEF DESCRIPTION OF THE DRAWINGS

For a more complete understanding of the present invention, reference is now made to the following detailed description of the embodiments illustrated in the accompanying drawings, wherein:

FIG. 1 is a sectional view of a sensor of a type suitable for flow-through operation;

FIG. 2 is a side elevational view of the sensor of FIG. 1 and a solenoid-operated valve connected to the opening at each end of the sensor;

FIG. 3 is a sectional view taken on line 3—3 of FIG. 1;

FIG. 4 is a sectional view taken on line 4—4 of FIG. 1;

FIG. 5 is an enlargement of one end of the structure illustrated in FIG. 2, with the solenoid-operated valve in section;

FIG. 6 is an enlargement of one end of an alternative structure having the sensor of FIG. 1 and a conductive screen assembly, with the conductive screen assembly in section;

FIG. 15 is a perspective view of a sensor having two parallel bar-like conductors and an outer shield;

FIG. 16 is a sectional view taken on line 16—16 of FIG. 15;

FIG. 17 is a sectional view taken on line 17—17 of FIG. 15;

FIG. 18 is an exploded perspective view of a portion of the sensor of FIG. 15;

FIG. 25 is an enlarged sectional view taken on line 25—25 of FIG. 23;

FIG. 26 is an enlarged side view of a portion of one end of the sensor of FIG. 25;

FIG. 27 is a sectional view taken on line 27—27 of FIG. 26;

DESCRIPTION OF PREFERRED EMBODIMENTS

Figure 7:
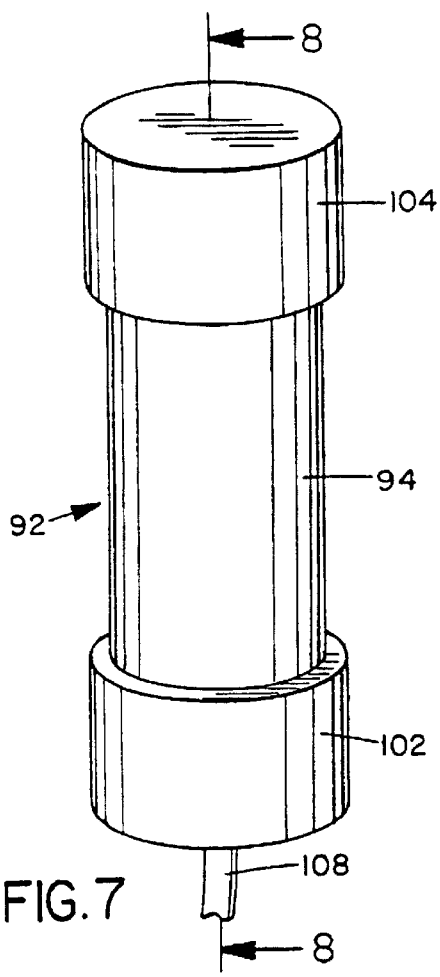
FIG. 7 is a perspective view of an alternative sensor of a type suitable for static operation.

As illustrated in FIGS. 1–4, a capacitive sensor 10 includes an elongated, generally tubular inner conductor 12 and an elongated, generally tubular outer conductor 14 that are coaxially or concentrically mounted with respect to one another. Conductors 12 and 14 are radially spaced from one another, thereby defining an elongated annular chamber 16. Outer conductor 14 includes two conductive endpieces 18 and 20, one threadably attached to each end of sensor 10. O-rings 21 and 23 seal endpieces 18 and 20, respectively, against leakage. Endpieces 18 and 20 have sensor inlet and outlet openings 22 and 24, respectively. As more fully described below, sensor 10 may be used to measure the volume charge density of a fluid, i.e., a liquid or gas in chamber 16, which may flow into sensor inlet opening 22 and out of sensor outlet opening 24.

Two body portions 26 and 28 made of a non-conductive material are disposed at opposite ends of sensor 10. Body portion 26 is fit within one end of outer conductor 14, and body portion 28 is fit within the other end of outer conductor 14. One end of inner conductor 12 is captured within an annular groove in body portion 26, and the other end is captured within an annular groove in body portion 28. Body portion 26 has an annular glue tang 30 that snaps into engagement with a corresponding annular groove 32 of body portion 28. This manner of attaching body portion 26 to body portion 28 facilitates economical assembly of the device.

Body portion 26 has three elongated arcuate fluid channels 38, 40 and 42 disposed at even spacings. Similarly, body portion 28 has three elongated arcuate fluid channels 44, 46 and 48 disposed at even spacings.

In operation, fluid is introduced into sensor inlet opening 22 in endpiece 18. The fluid enters chamber 16 through fluid channels 38, 40 and 42. The flow exits chamber 16 through fluid channels 44, 46 and 48. Sensor outlet opening 24 in endpiece 20 receives the fluid flow.

Although body portions 26 and 28 insulate the fluid in chamber 16 from electrical contact with inner and outer conductors 12 and 14, in other embodiments the inner and outer conductors may be coated with a suitable dielectric material to insulate them from the fluid. In still other embodiments (not shown), the inner and outer conductors may be coatings of conductive material deposited on concentric tubes made of glass or other insulating material. Although many such embodiments and variations will occur to those skilled in the art in view of these teachings, the common concept among them is that a fluid introduced into a chamber between two conductors and electrically insulated from the conductors by an insulating or dielectric material defines a capacitance.

In other embodiments (not shown), additional chambers may be included concentrically with one another to increase the capacitance of the sensor. In other words, although in the illustrated embodiment the combination of inner and outer conductors 12 and 14 and body portions 26 and 28 define a single chamber 16 electrically illustrated from conductors 12 and 14, in other embodiments additional insulators and conductors arranged in a concentric manner may define additional such chambers.

A coaxial cable 50 electrically connects sensor 10 to the circuitry described below. One end of cable 50 is stripped to expose or bare the center conductor 52. Center conductor 52 is soldered to the inside surface of inner conductor 12. The shield 54 of cable 50 is bared where cable 50 enters outer conductor 14. Nevertheless, cable 50 has shield 54 all along its length between sensor 10 and the associated electronic circuit. A collet 56 secures cable 50 to outer conductor 14 and also makes an electrical connection between outer conductor 14 and shield 54. Cable 50 is preferably not bared between collet 56 and the point at which center conductor 52 is soldered to inner conductor 12 to maximize signal shielding inside sensor 10.

In other embodiments (not shown), some or all of the circuitry described below may be disposed inside the sensor. For example, in certain sensors the capacitance may be so low that the parasitic capacitance of the coaxial cable may affect the sensitivity of the system. Therefore, it may be desirable to dispose at least some of the electronic circuit components inside the sensor rather than externally to it. In certain such embodiments, all of the circuitry may be disposed inside the sensor, and the sensor may include an integral display for indicating the capacitance.

It is important that outer conductor 14, its endpieces 18 and 20, and even collet 56 all be made of a suitable conductive material such as metal and conductively coupled to one another and grounded to promote complete shielding of chamber 16 against external electric fields. As a result of this shielding, the only way for any external electric field to enter would be via openings 22 and 24.

An additional feature that shields against intrusion of external electric fields in certain embodiments comprises screens 34 and 36 disposed in endpieces 18 and 20, respectively. Screens 34 and 36 are made of a conductive material such as woven metal wire that shields against entry of external electric fields during operation. Screens 34 and 36 are preferably conical and have a weave that is sufficiently close to block electric fields to the extent desired, yet sufficiently coarse to permit the desired flow rate through sensor 10.

Other features may be included in addition to or alternatively to those described above to shield against external electric fields. As illustrated in FIGS. 2–3, in one embodiment of the invention solenoid-operated valve assemblies 58 and 60 seal openings 20 and 22, respectively, during operation. Assemblies 58 and 60 include valve cylinders 62 and 64, respectively, that are coupled to the female-threaded ends of endpieces 18 and 20. As illustrated in FIG. 5, a male-threaded end of valve cylinder 62 is coupled to the female-threaded end of endpiece 18. A male-threaded end of a solenoid 66 is in turn coupled to a female-threaded end of valve cylinder 62 opposite its male-threaded end. A valve inlet opening 68 in valve cylinder 62 communicates fluid with sensor 10 under control of solenoid 66. Solenoid 66 includes a coil 70 and a magnetic plunger 72 arranged in the conventional manner of a solenoid. A ring 74 frictionally fit onto plunger 72 and an elastomeric bumper 76, such as an O-ring, limit the travel of plunger 72. A valve stem 78, made of a suitable conductive material, is mounted on the distal end of plunger 72. In operation, when solenoid 66 is activated by energizing coil 70, plunger 72 moves toward valve cylinder 62, urging the distal end of valve stem 78 into sealing contact with a valve seat 80 in valve cylinder 62. The distal end of valve stem 78 may be beveled or chamfered, and valve seat 80 may be correspondingly beveled or chamfered to promote sealing. When solenoid 66 is activated, valve stem 78 is not in sealing contact with valve seat 80, thereby allowing a fluid received through valve inlet 68 to flow into sensor 10. Solenoid-operated valve 64 has a structure identical to that of solenoid-operated valve 62 and is therefore not shown in similar detail.

It should be noted that valve cylinder 62 and valve stem 78 are both made of electrically conductive materials and are electrically coupled to each other as well as outer conductor 14. Thus, when solenoid 66 is activated, thereby closing solenoid-operated valve 58, no external electric field can penetrate into sensor 10.

Although FIGS. 2, 5 and 6 illustrate valve assemblies 58 and 60 oriented with respect to sensor 10 such that the outflow of fluid through outlet opening 24 is directed toward the distal end of valve stem 78, such an orientation is illustrated for purposes of convenience. If, for example, the fluid pressure is expected to be significant, it may be desirable to provide an alternative valve assembly (not shown) such that the valve stem is oriented perpendicularly to the outflow to minimize the likelihood that the pressure may force the valve open.

In an alternative embodiment, illustrated in FIG. 6, an electric field (E-field) blocking adapter 84 may be coupled to sensor 10. E-field blocking adapter 84 retains within it a screen 82 made of an electrically conductive material that shields against entry of external electric fields during operation. Screen 82 is preferably conical and has a weave that is sufficiently close to block electric fields to the extent desired, yet sufficiently coarse to permit the desired flow rate through sensor 10. Adapter 84 includes first and second adapter portions 86 and 88. A male-threaded end of first adapter portion 86 is coupled to the female-threaded end of endpiece 18. A male-threaded end of second adapter portion 88 is coupled to the female-threaded end of first adapter portion 86 at the opposite end of first adapter portion 86. Screen 82 is retained between first and second adapter portions 86 and 88. A female-threaded end of an adapter inlet 90 is coupled to a male-threaded end of second adapter portion 88. Although not shown for purposes of clarity, an identical E-field blocking adapter 84 may be coupled to endpiece 20. E-field blocking adapter 84 may be included in the invention as an alternative to solenoid-operated valve 58 or, in certain embodiments, in addition to solenoid-operated valve 58.

In other embodiments (not shown), alternative means may be used to mechanically block external E-fields. For example, a spring-loaded cap may be used in a manner similar to adapter 84. Any such means would be suitable so long as it makes electrical contact with outer conductor 14.

As illustrated in FIGS. 7–10, an alternative capacitive sensor 92 includes an elongated, generally tubular outer conductor 94 and an elongated, generally tubular inner conductor 96. A tubular insulator 98 made of glass, plastic or similar suitable material radially spaces conductors 94 and 96 from one another, thereby defining an elongated annular chamber 100. Inner conductor 96 extends into a well in the end of insulator 98 that extends into chamber 100. Insulator 98 prevents electrical conduction between conductors 94 and 96 in the presence of a fluid or other material to be measured in chamber 100. Outer conductor 94 includes two conductive endpieces 102 and 104, one at each end of sensor 92. Endpieces 102 and 104 are female-threaded and couple to the male-threaded ends of the tubular portion of outer conductor 94. Endpiece 104 may be removed to fill chamber 100 with a fluid.

The central conductor 106 of a coaxial cable 108 is soldered or friction-fit inside a longitudinal bore in inner conductor 96. The shield 110 of coaxial cable 108 is retained between a frusto-conical shoulder 112 in the opening in endpiece 102 through which cable 108 extends and a correspondingly frusto-conical projection 114 in the end of the tubular portion of outer conductor 94. Because shield 110, endpiece 102, and outer conductor 94 are all electrically conductive and in contact with one another, they are all at the same ground potential and provide shielding against external electric fields.

It should be noted that with respect to each of the sensor embodiments described above, all of the electrically conductive elements are preferably made of similar metals to avoid electrolytic corrosion. Furthermore, the metals should be resistant to corrosion by the fluid with which the sensor is used. Stainless steel, copper, and brass may thus be highly suitable metals for these elements. Furthermore, an insulator (internal coating or insulating wall) may be included to protect all metal that would otherwise be in contact with fluid from a half reaction of electroplating caused by the electric fields. As persons skilled in the art will appreciate, the nearest point allowable for metal contact with fluid depends primarily on the voltage applied to the inner plate, the distance that the metal-fluid contact point is from the inner conductor, the electrode potential of the metal, and the quantity and species of ions present in the fluid.

Figure 8:
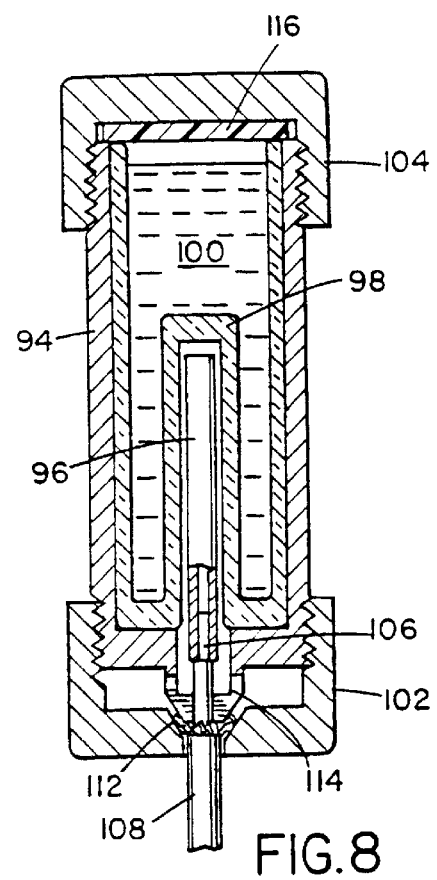
FIG. 8 is a sectional view taken on line 8—8 of FIG. 7.
Figure 9:
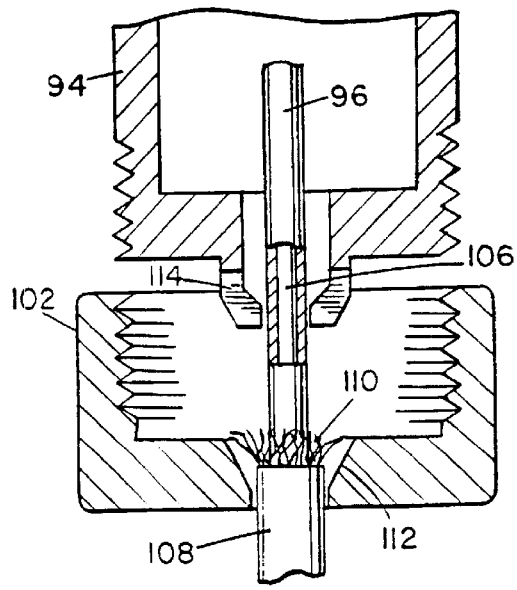
FIG. 9 is an enlarged sectional view of a portion of FIG. 8, showing the assembly of the end cap, the inner conductor, and the outer conductor.
Figure 10:
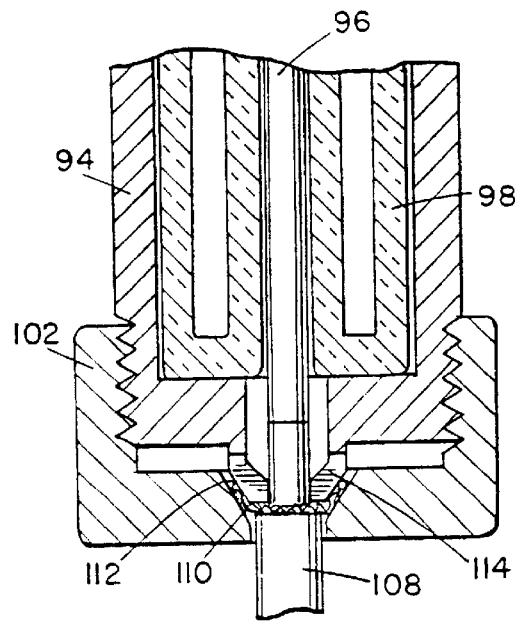
FIG. 10 is an enlarged sectional view of the assembled sensor of FIG. 8.

As more fully described below in connection with a preferred circuit, sensor 92 may be used to measure the volume charge density of a fluid. A user may unscrew endpiece 104 and fill chamber 100 with fluid. The user then replaces endpiece 104, screwing it onto the distal end of the tubular portion of outer conductor 94 to secure it. A gasket 116 between endpiece 104 and the distal end of the tubular portion of outer conductor 96 seals chamber 100 against fluid leakage. Nevertheless, when sensor 92 is filled with fluid, it is preferable to maintain it in a vertical position, as illustrated in FIG. 8. With endpieces 102 and 104 secured, chamber 100 is completely shielded against penetration of external electric fields.

Figure 11:
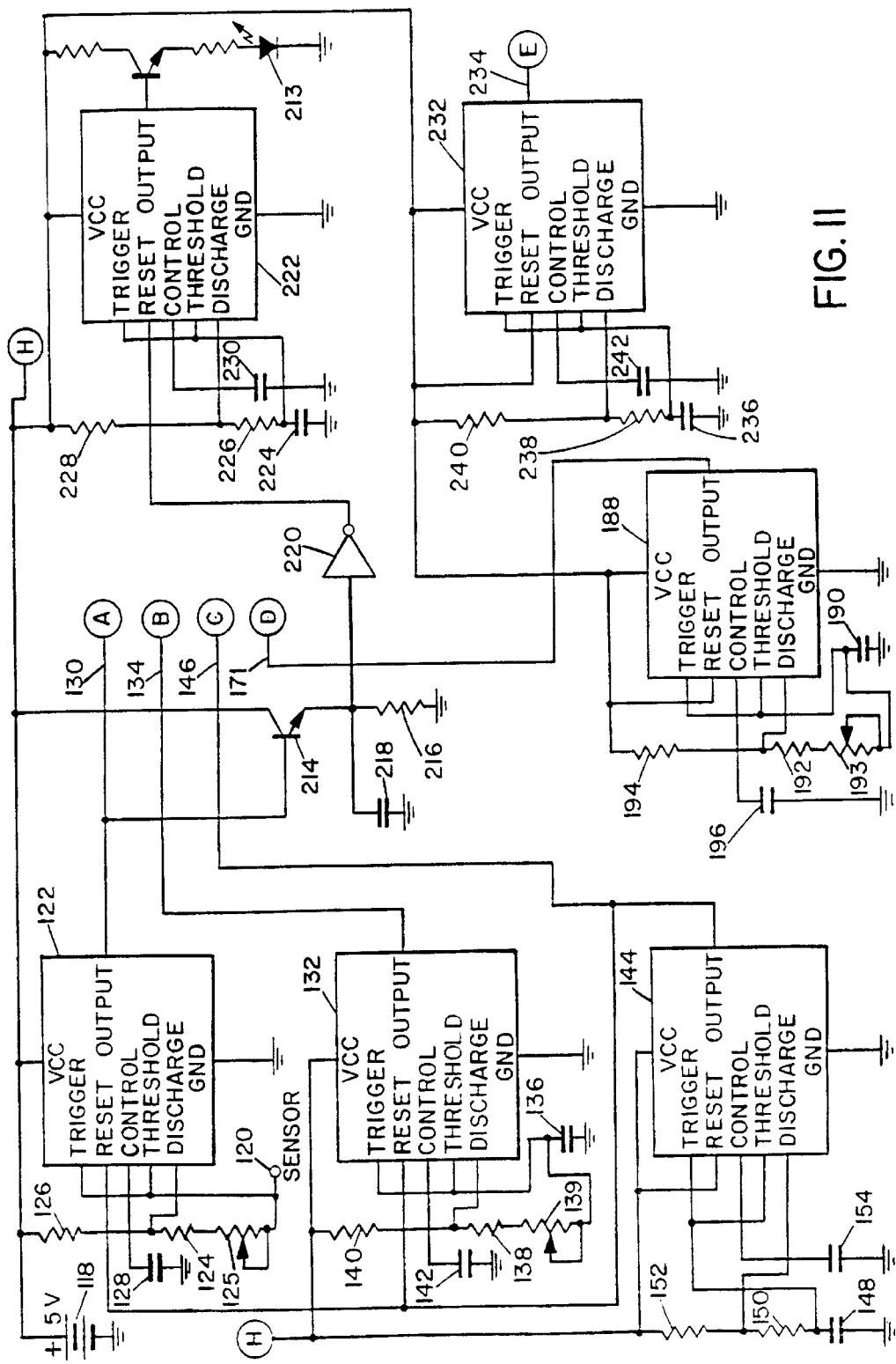
FIG. 11 is a portion of a schematic diagram illustrating a portion of a circuit for measuring volume charge density that subtracts a measured test frequency from a predetermined reference frequency.
Figure 12:
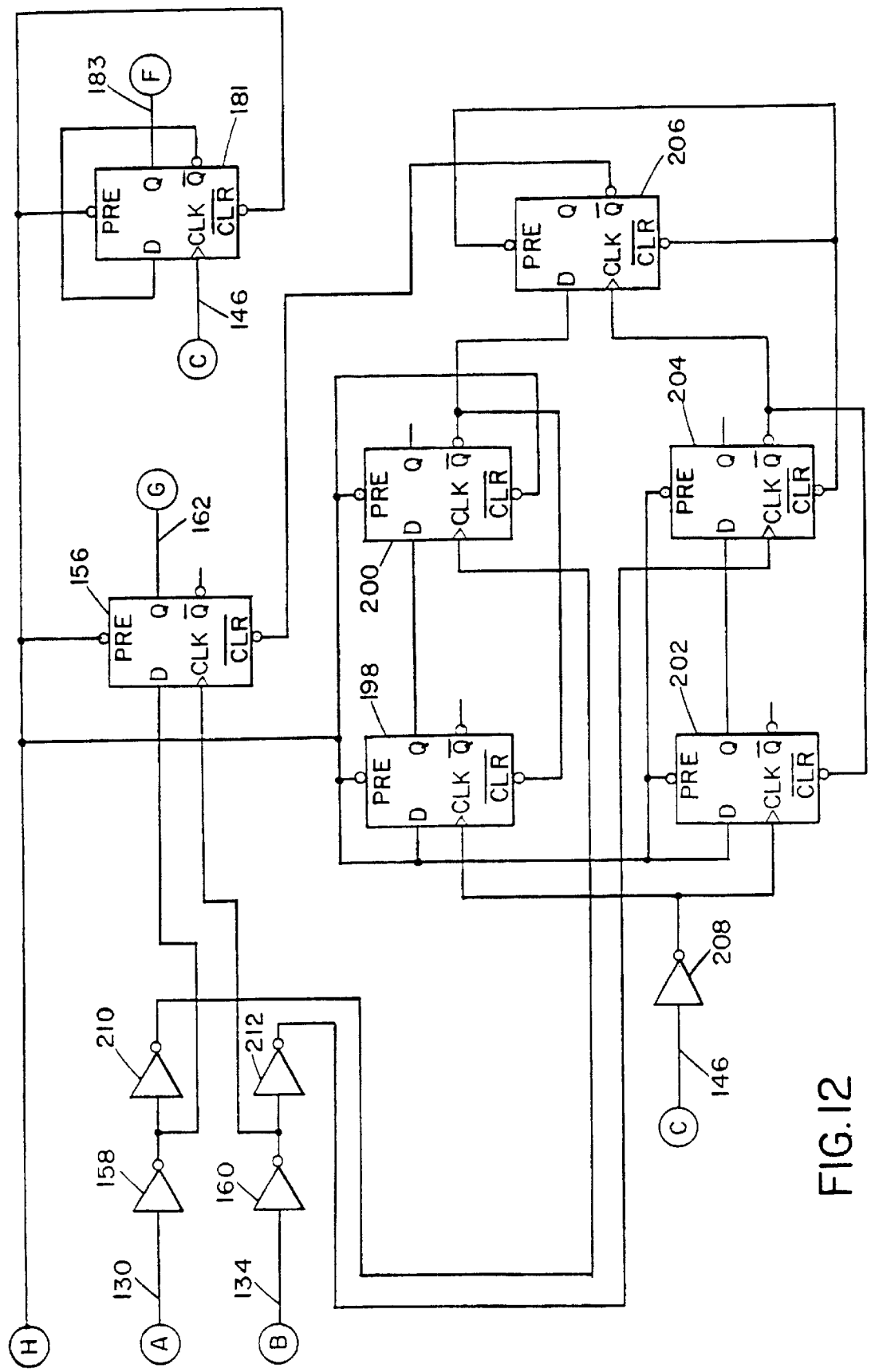
FIG. 12 is a first continuation sheet of the schematic diagram of FIG. 11 illustrating another portion of the circuit.
Figure 13:
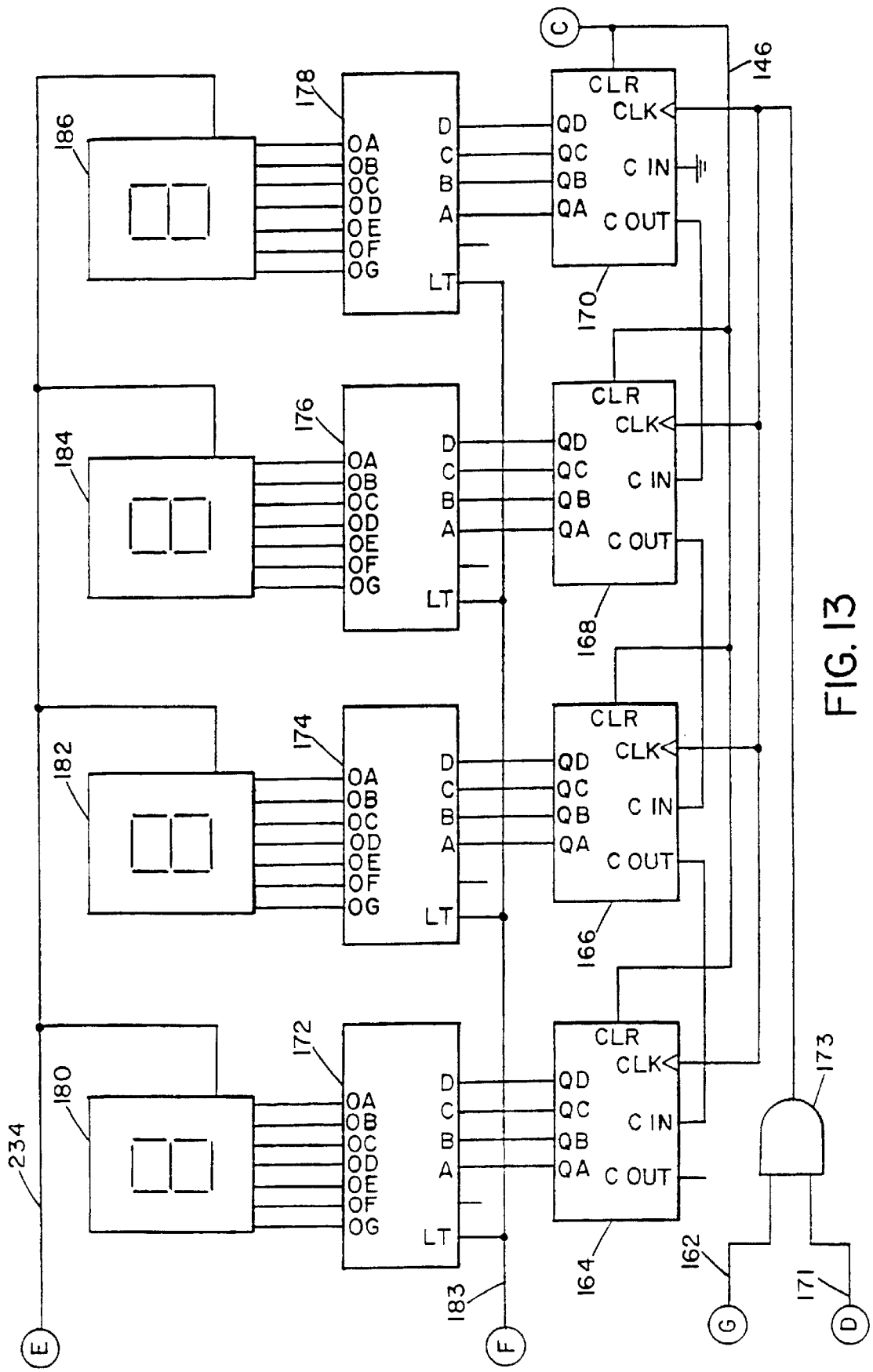
FIG. 13 is second continuation sheet of the schematic diagram of FIGS. 11–12 illustrating still another portion of the circuit.

FIGS. 11–13 illustrate a volume charge density measuring circuit that may be connected to a capacitive sensor, such as sensor 10 or sensor 92. A suitable power source, represented by a battery 118, provides a power supply voltage (+5V) with respect to ground. The inner and outer conductors of the sensor function as the plates of a capacitor. The outer conductor of sensor 10 or 92 is grounded, as described above. The inner conductor of sensor 10 or 92 is coupled to a connector 120.

Connector 120 is coupled to the THRESHOLD and TRIGGER inputs of a 555-type timer chip 122 configured as a free-running oscillator. Two resistors 124 and 125 are connected in series with one another between connector 120 and the DISCHARGE input of timer chip 122. Resistor 125 is a variable resistor that facilitates the calibration procedure described below. Another resistor 126 is connected between the DISCHARGE input of timer chip 122 and the power supply voltage. A capacitor 128 is connected between the CONTROL input of timer chip 122 and ground. The TRIGGER and THRESHOLD inputs are connected to one another. The RESET input is connected in the manner described below. Timer chip 122 generates a test signal 130 at its output (OUTPUT) that has a frequency inversely proportional to the capacitance of the sensor to which the circuit is connected via connector 120. The R-C time constant defined by the capacitance of the sensor and the resistance of resistors 124 and 125 thus determine the frequency of test signal 130.

A second 555-type timer chip 132 configured as a free-running oscillator generates at its output (OUTPUT) a reference signal 134 that has a frequency proportional to the value of a capacitors 136, the first terminal of which is coupled to the THRESHOLD and TRIGGER inputs. The second terminal of capacitor 136 is connected to ground. Two resistors 138 and 139 are connected in series with one another between the first terminal of capacitor 136 and the DISCHARGE input of timer chip 132. Resistor 139 is a variable resistor that facilitates the calibration procedure described below. The R-C time constant defined by capacitor 136 and resistors 138 and 139 thus determine the frequency of reference signal 134. Another resistor 140 is connected between the DISCHARGE input of timer chip 132 and the power supply voltage. A capacitor 142 is connected between the CONTROL input of timer chip 132 and ground. The RESET input is connected in the manner described below.

A third 555-type timer chip 144 configured as a free-running oscillator generates at its output (OUTPUT) a trigger signal 146 that has a frequency proportional to the value of a capacitor 148, the first terminal of which is coupled to the THRESHOLD and TRIGGER inputs. The second terminal of capacitor 148 is connected to ground. A resistor 150 is connected between the first terminal of capacitor 148 and the DISCHARGE input of timer chip 144. The R-C time constant defined by capacitor 148 and resistor 150 thus determines the duty cycle of trigger signal 146. A duty cycle that produces a pulse of sufficiently short duration not to inhibit the measurement is preferred. Another resistor 152 is connected between the DISCHARGE input of timerchip 144 and the power supply voltage. A capacitor 154 is connected between the CONTROL input of timer chip 144 and ground. The RESET input is connected to the power supply voltage. Trigger signal 146 is provided to the RESET inputs of timer chips 122 and 124.

It should be noted that 555-type timers are used in these embodiments because they are economical and readily available commercially. Nevertheless, other timer circuits may be used if higher frequency operation or extreme accuracy is desired. Furthermore, the free-running oscillators described above are preferred over alternative circuits such as one-shot circuits because the capacitance values of the sensor may be small, thereby degrading the signal if one-shots are used. Conventional timer chips, such as 555 timers, are more tolerant of small capacitance values when configured to operate as free-running oscillators than when configured to operate as one-shots.

Although the operation of the circuit is described in further detail below, broadly stated, the circuit determines the frequency difference between test signal 130 and reference signal 134 by subtracting one signal from the other. Test signal 130 is coupled to the D input of a D-type monostable multivibrator or flip-flop 156 (FIG. 12), and reference signal 134 is coupled to the clock (CLK) input. Schmitt-trigger inverters 158 and 160 shape signals 130 and 134, respectively, to provide cleaner squarewaves at the D and CLK inputs of flip-flop 156. Flip-flop 156 performs the subtraction, producing at its Q output a difference signal 162 having a frequency that represents the difference between the frequencies of signals 130 and 134. A potential problem arises because difference signal 162 only accurately represents the difference frequency when test signal 130 and reference signal 134 are less than 180 degrees out-of-phase. Chip 144 synchronizes timer chips 122 and 132 by periodically resetting them simultaneously to prevent them from drifting too far out of phase. The period of trigger signal 146 should thus be greater than the periods of test signal 130 and reference signal 134, preferably several hundred or even several thousand times greater. It should be noted that the frequency of difference signal 162 is inversely proportional to the capacitance of the sensor in this embodiment.

Difference signal 162 is provided to a suitable display circuit. Although a preferred digital display circuit is illustrated in FIG. 13, any circuit that produces an indication corresponding to the measured capacitance would be suitable. In the illustrated circuit, difference signal 162 is coupled to four cascaded four-bit counter chips 164, 166, 168 and 170 via one input of a two-input AND gate 173. As described further below, a gain signal 171 is provided to the other input of AND gate 173 to facilitate calibration of the display circuit. The frequency of gain signal 171 determines the number of pulses that AND gate 173 allows to occur during each time difference slot, as described further below with regard to a calibration procedure. The output of AND gate 173 is provided to the clock (CLK) input of each of counter chips 164, 166, 168 and 170. The outputs of counter chips 164, 166, 168 and 170 are provided to four binary-coded decimal (BCD)-to-seven segment decoder/drivers 172, 174, 176 and 178, each of which in turn drives one of four single-digit seven-segment displays 180, 182, 184 and 186. A display latch signal, 183 is generated by a flip-flop 181 (FIG. 12) in response to trigger signal 146 and provided to each of decoder/drivers 172, 174, 176 and 178.

The circuit may be calibrated in any suitable manner, such as that described below. Thus, displays 180, 182, 184 and 186 may display a four-digit measurement of parts-per-million or parts-per-billion of dissolved solids. As noted above, gain signal 171 is used to calibrate the circuit. A 555-type timer chip 188 (FIG. 11) configured as a free-running oscillator produces gain signal 171, which has a frequency proportional to the value of a capacitor 190, the first terminal of which is coupled to the THRESHOLD and TRIGGER inputs. The second terminal of capacitor 190 is connected to ground. Two resistors 192 and 193 are connected in series with one another between the first terminal of capacitor 190 and the DISCHARGE input of timer chip 188. Resistor 193 is a variable resistor that facilitates the calibration procedure described below. The R-C time constant defined by capacitor 190 and resistors 192 and 193 thus determine the frequency of gain signal 171. Another resistor 194 is connected between the DISCHARGE input of timer chip 188 and the power supply voltage. A capacitor 196 is connected between the CONTROL input of timer chip 188 and ground. The RESET input is connected to the power supply voltage.

The circuit further includes a clamping circuit that clamps difference signal 162 to a zero frequency when test signal 130 has a frequency greater than that of reference signal 134. The circuit is preferably configured so that the display indicates a measurement of zero when test signal 130 has a frequency equal to that of reference signal 134. The display indicates a higher measurement when test signal 130 has a frequency lower than that of reference signal 134. The problem that the clamping circuit addresses is ensuring that the display indicates a measurement only when the sign of the frequency difference between the reference frequency and the test frequency is positive, i.e., when test signal 130 has a frequency lower than that of reference signal 134 from which it is subtracted. Absent the clamping circuit, when the frequencies of test signal 130 and reference signal 134 are close to one another, fluctuations that result in test signal 130 having a frequency higher than that of reference signal 134 would result in the display of an erroneous value.

The clamping circuit includes five D-type flip flops 198, 200, 202, 204 and 206. Flip-flops 198 and 200 are config- ured as a circuit often referred to as a "one-and-only-one circuit." Flip-flops 202 and 204 are also configured as a "one-and-only-one circuit." The clock (CLK) inputs of flip-flops 198 and 202 are coupled to trigger signal 146 via a Schmitt-trigger inverter 208. The D inputs of flip-flops 198 and 200 are coupled to the supply voltage. Each time trigger signal 146 is asserted, the Q outputs of flip-flops 198 and 200 produce a high signal. The Q output of flip-flop 198 is coupled to the D input of flip-flop 200. Similarly, the Q output of flip-flop 202 is coupled to the D input of flip-flop 204. The clock input of flip-flop 200 is coupled to test signal 130 via inverter 158 and another inverter 210. Similarly, the clock input of flip-flop 204 is coupled to reference signal 134 via inverter 160 and another inverter 212.

It should be noted that in other embodiments (not shown), one-and-only-one circuits may be cascaded to provide higher resolution. The resulting circuit may be referred to as, for example, a two-and-only-two or a three-and-only-three circuit.

In response to a high signal at the Q output of flip-flop 198, flip-flop 200 produces a low signal at its Q output on the next rising edge of test signal 130. Because the Q output is also coupled to the clear (CLR) input of flip-flop 198, flip-flop 198 is cleared in response to that rising edge. Thus, the output of flip-flop 200 in response to assertion of trigger signal 146 consists of exactly one cycle of test signal 130. Similarly, in response to a high signal at the Q output of flip-flop 202, flip-flop 204 produces a low signal at its Q output on the next rising edge of reference signal 134. Because the Q output is also coupled to the clear (CLR) input of flip-flop 202, flip-flop 202 is cleared in response to that rising edge. Thus, the output of flip-flop 204 in response to assertion of trigger signal 146 consists of exactly one cycle of reference signal 134.

The D input of flip-flop 206 is coupled to the Q output of flip-flop 200, and the CLK input of flip-flop 206 is coupled to the Q output of flip-flop 204. Flip-flop 206 thus compares one cycle of test signal 130 to one cycle of reference signal 146. If reference signal 134 has a frequency lower than that of test signal 130, i.e., one cycle of reference signal 134 is longer than one cycle of test signal 130, flip-flop 206 produces a low signal at its Q output. The CLR input of flip-flop 156 is coupled to the Q output of flip-flop 206. Thus, flip-flop 156 is held in a cleared state so long as reference signal 134 has a frequency lower than that of test signal 130.

The circuit further includes an error indicator circuit that produces an error indication when the frequency of test signal 130 is zero. Test signal 130 may go to zero if the circuit malfunctions or the sensor is damaged. For example, if insulator 98 of sensor 92 (FIGS. 7–10) breaks, the fluid in chamber 100 may create a conductive path between conductors 94 and 96. Test signal 130 would go to ground if a conductive path exists between conductors 94 and 96. The error detection circuit includes a light-emitting diode (LED) 213 that flashes when such a short-circuit between the inner and outer conductors of a sensor occurs.

The error indicator circuit includes a transistor 214, a resistor 216 and a capacitor 218 (FIG. 11). The collector of transistor 214 is coupled to the supply voltage; the base is coupled to test signal 130, and the emitter is coupled to one terminal of resistor 216 and one terminal of capacitor 218. The other terminals of resistor 216 and capacitor 218 are coupled to ground. Test signal 130 charges capacitor 218. Resistor 216 discharges capacitor 218 more slowly than test signal 130 charges it. Thus, the voltage on capacitor 218 remains above the value corresponding to a high logic level (typically about 2.5 volts for chips having transistor-transistor logic (TTL), although CMOS or any other chip technology would be suitable). In inverter 220 coupled to capacitor 218 produces a low output. When test signal 130 ceases to charge capacitor 218, it quickly discharges through resistor 216. When the voltage on capacitor 218 drops below the value corresponding to a low logic level (typically about 1.7 volts for TTL), inverter 220 produces a high output. The output of inverter 220 is coupled to the RESET input of a 555-type timer chip 222 that is configured as a free-running oscillator. Timer chip 222 causes LED 213 to flash. The flashing rate or cycle time is determined by the value of a capacitor 224 and a resistor 226. The first terminal of capacitor 224 is coupled to the THRESHOLD and TRIGGER inputs of timer chip 222. The second terminal of capacitor 224 is connected to ground. Resistor 226 is connected between the first terminal of capacitor 224 and the DISCHARGE input of timer chip 222. Another resistor 228 is connected between the DISCHARGE input of timer chip 222 and the power supply voltage. A capacitor 230 is connected between the CONTROL input of timer chip 222 and ground. Thus, so long as the RESET input is high, timer chip 222 produces one pulse at its output each cycle time.

The remaining circuitry relates to the display. Another 555-type timer chip 232 is configured as a free-running oscillator that produces a strobe signal 234. In response to strobe signal 234, displays 180, 182, 184 and 186 are activated at a rate determined by the value of a capacitor 236 and a resistor 238 The first terminal of capacitor 236 is coupled to the THRESHOLD and TRIGGER inputs of timer chip 232 The second terminal of capacitor 236 is connected to ground. Resistor 238 is connected between the first terminal of capacitor 236 and the DISCHARGE input of timer chip 232 Another resistor 240 is connected between the DISCHARGE input of timer chip 232 and the power supply voltage. A capacitor 242 is connected between the CONTROL input of timer chip 232 and ground.

In operation, timer chip 122, configured as a free-running test oscillator, produces test signal 130, which has a frequency inversely proportional to the capacitance of the sensor to which the circuit is coupled, such as sensor 10, sensor 92 or other suitable capacitive sensor. The capacitance is responsive to the dielectric constant or volume charge density of the fluid or other sample contained with the sensor. Timer chip 132, configured as a free-running reference oscillator, produces reference signal 134, which has an essentially constant or fixed frequency. Timer chip 144, configured as a free-running trigger oscillator, produces trigger signal 146, which periodically simultaneously resets timer chips 122 and 132 to synchronize them.

In response to test signal 130 and reference signal 134, an indicator circuit provides a user with an indication, such as a digitally displayed value, that represents the sensor capacitance. Although the indicator circuit includes a digital display in the illustrated embodiment, in other embodiments (not shown) the indicator circuit may include a binary indicator that indicates only a "Go" or "No-go" condition.

Flip-flop 156 produces difference signal 162, which has a frequency equal to the frequency difference between test signal 130 and reference signal 134. A clamping circuit, which includes two one-and-only-one circuits, ensures that flip-flop 156 responds only when the sign of difference signal 162 is positive, i.e., when test signal 130 has a frequency less than that of reference signal 134. The clamping circuit clamps difference signal 162 to zero when test signal 130 has a frequency greater than that of reference signal 134. The indicator circuit also includes cascaded counters 164, 166, 168 and 170 that produce a count in response to difference signal 162. Trigger signal 146 periodically resets the count. A digital display produces a numeric value corresponding to the count.

Figure 14:
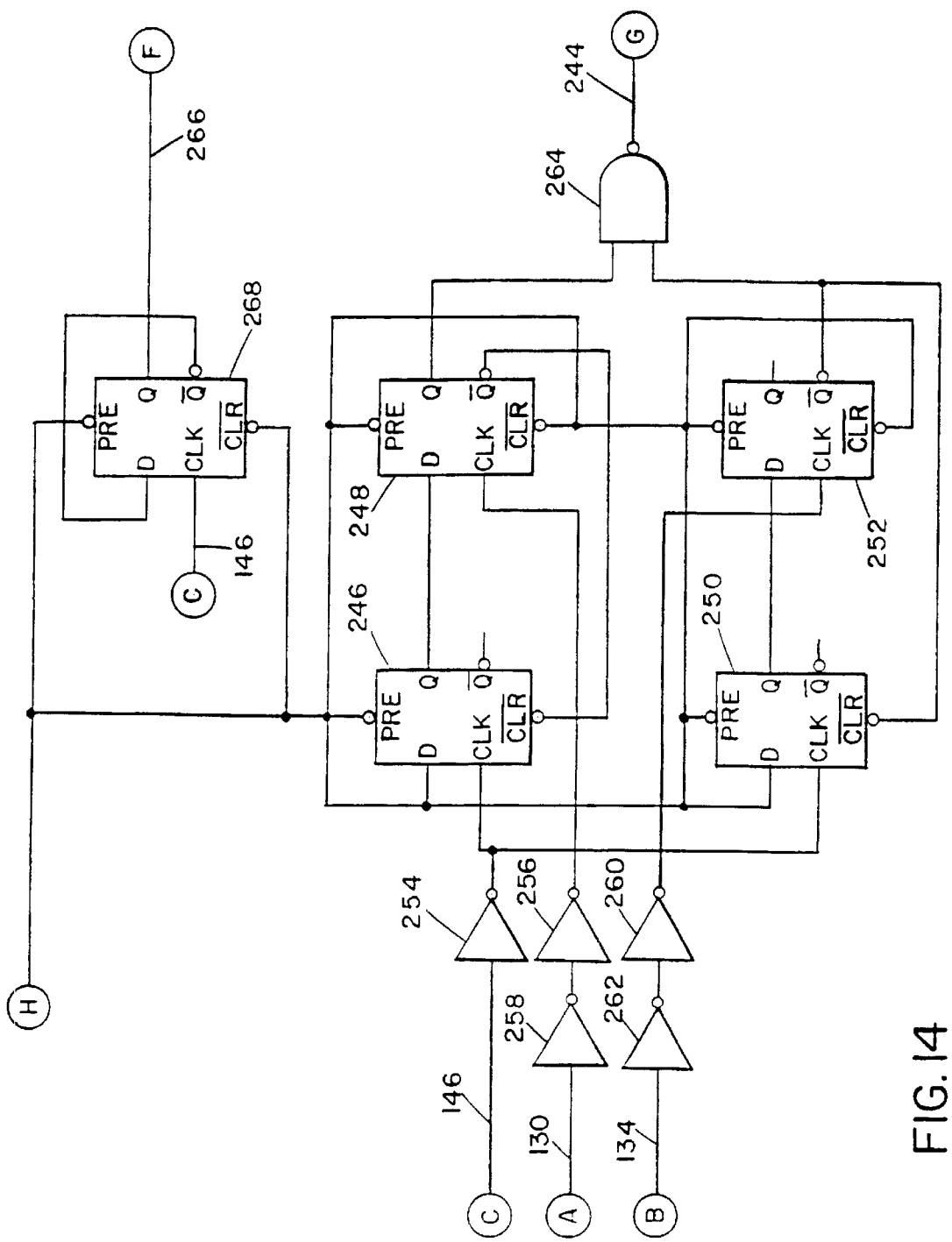
FIG. 14 is a portion of a schematic diagram illustrating an alternative portion of the circuit that may be used in place of that illustrated in FIG. 12.
Figure 19:
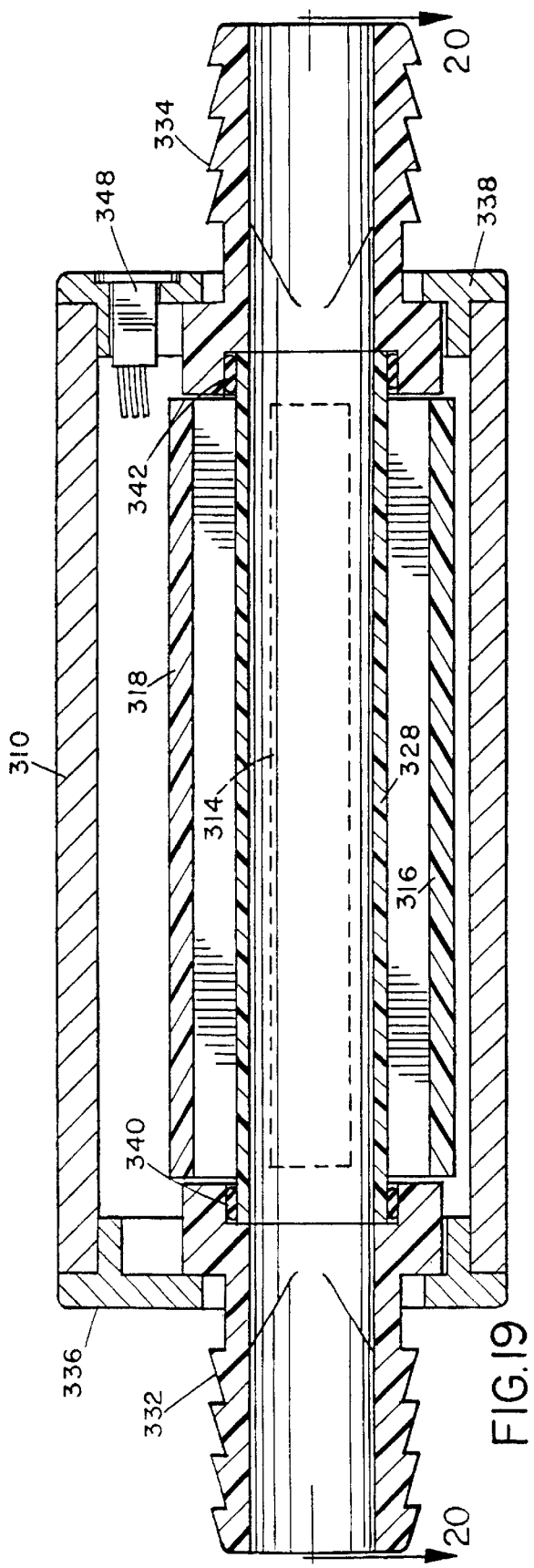
FIG. 19 is a sectional view taken on line 19—19 of FIG. 15.
Figure 20:
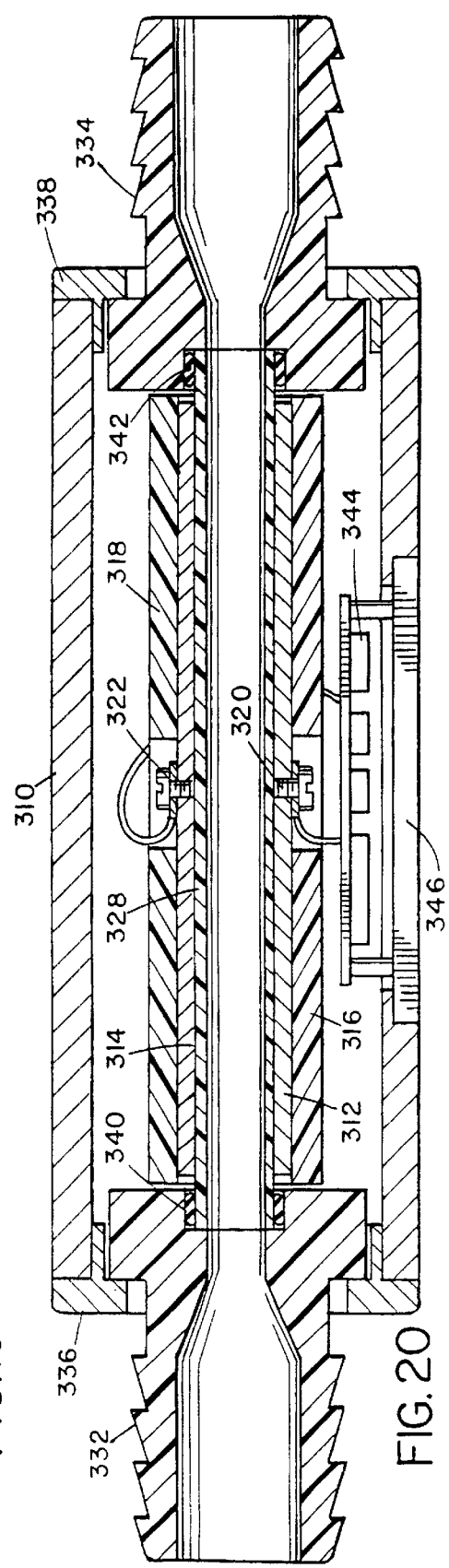
FIG. 20 is a sectional view taken on line 20—20 of FIG. 19.

FIG. 14 illustrates an alternative portion of the circuit described above that may be included in place of the portion illustrated in FIG. 12. The essence of this alternative circuit is that it provides a difference signal 244 that has a frequency directly proportional to the capacitance of the sensor, which may be desirable depending, upon the type, of measurements to be taken and the meaning the user assigns to the measurements. In contrast, in the embodiment described above, difference signal 162 has a frequency inversely proportional to the capacitance of the sensor.

In contrast to the circuit described above, signal 130 is coupled directly to two one-and-only-one circuits, one of which includes two D-type flip flops 246 and 248, and the other of which includes two D-type flip-flops 250 and 252. The clock (CLK) inputs of flip-flops 246 and 250 are coupled to trigger signal 146 via a Schmift-trigger inverter 254. The D inputs of flip-flops 246 and 250 are coupled to the supply voltage. The Q output of flip-flop 246 is coupled to the D input of flip-flop 248. Similarly, the Q output of flip-flop 250 is coupled to the D input of flip-flop 252. The clock input of flip-flop 248 is coupled to test signal 130 via inverters 256 and 258. Similarly, the clock input of flip-flop 252 is coupled to reference signal 134 via inverters 260 and 262.

The Q output of flip-flop 248 is coupled to one input of an AND gate 264. The Q output of flip-flop 248 is coupled to the CLR input of flip-flop 246. The a output of flip-flop 252 is coupled to the other input of AND gate 264 and to the CLR input of flip-flop 250. The Q output of flip-flop 252 is not connected. The output of AND gate 264 is difference signal 244.

The circuit portion illustrated in FIG. 14 generates a display latch signal 266 in the same manner as the circuit portion illustrated in FIG. 12 generates display latch signal 183. Specifically, a flip-flop 268 generates display latch signal 266 in response to trigger signal 146 and provides it to each of decoder/drivers 172, 174, 176 and 178 (FIG. 13).

A user may perform a calibration procedure prior to beginning measurement or at the time the system is manufactured. The user introduces a reference sample, such as double-distilled water, into the sensor chamber. The user then adjusts resistor 193 to increase the frequency of gain signal 171. As noted above, gain signal 171 determines the number of pulses that occur per time difference slot. The time difference slot is the interval between the clearing of the one-and-only-one circuit to which test signal 130 is coupled and the one-and-only-one circuit to which reference signal 134 is coupled. The resolution of the digital display is responsive to the number of such pulses that occur within the time difference slot. For example, if it is desired to measure between one and 2500 parts per million of impurities in a sample, the user may desire to adjust gain signal 171 such that 2500 pulses occur in the time difference slot. The user then adjusts resistor 139 until the displayed value reaches zero. The user introduces into the sensor chamber a sample of a material having the highest impurity density expected to be measured. With that sample still in the sensor chamber, the user adjusts resistor 193 until the display indicates the desired value. For example, the user may adjust resistor 193 to cause the display to indicate the volume charge density of the sample if it is known.

The measurements obtained using the present invention are more accurate than those obtained using prior measuring systems because the preferred sensor is essentially completely shielded against external electric fields during operation. In addition, the novel circuitry of the present invention is more economical than the circuitry of prior capacitive measuring systems.

As illustrated in FIGS. 15–20, an alternative capacitive sensor 300 includes an elongated, generally tubular electrically conductive body 310 that functions as shield against external electric fields. Enclosed inside body 310 and thus protected against the effects of such fields are two parallel, elongated, bar-like conductors 312 and 314. Conductors 312 and 314 form part of a conductor assembly (FIGS. 17–18) that includes two interlocking generally semicylindrical retainer halves 316 and 318. Screws 320 and 322 fasten conductors 312 and 314 to retainer halves 316 and 318, respectively, and provide a connection point for electrical wires 324 and 326, respectively. Also captured between retainer halves 316 and 318 and between conductors 312 and 314 is a non-conductive tube 328. Tube 328 defines the chamber into which the fluid or other material sample (not shown) is introduced for measurement. As in the sensor embodiments described above, it is important to insulate the conductors from the chamber and/or one another to prevent electrical conduction between them through the fluid. Although tube 328 provides such insulation, conductors 312 and 314 could alternatively be coated with a suitable dielectric material. A small screw 330, preferably plated with a highly conductive material such as gold, extends through one of halves 316 and 318 and protrudes into the interior of tube 328, thus making electrical contact with the material sample. Screw 330 may be electrically coupled to body 310, as shown, or alternatively may be electrically coupled to one of conductors 312 and 314, as indicated in dashed line. If coupled to body 310, body 310 is preferably in turn coupled chassis ground, i.e., earth ground. The function of screw 330 is described further below with respect to the electronics.

Ports 332 and 334 allow a fluid material sample to flow through the chamber. Ports 332 and 334 are retained in endpieces 336 and 338, respectively, and capture the conductor assembly between them. O-rings 340 and 342 provide seals between the conductor assembly and ports 332 and 334. Although ports 332 and 334 are illustrated as having hose barbs, they may have any other suitable attachment mechanism, such as threads. Endpieces 336 and 338 are friction-fit into the ends of body 310 and are made of an electrically conductive material to extend the shielding to the ends of sensor 300.

Also enclosed inside body 310 and thus shielded against external electric fields is sensor electronics 344, including a digital display 346. Display 346 has a window that fits within an opening in body 310 and thus allows a user to read the displayed value representing the measured quantity. Electronics 344 may comprise any of the circuitry described above, or any of the alternative circuitry described below. A multiple-pin connector 348 fits within an opening in body 310 and provides signals for external data acquisition devices or test equipment (not shown).

Figure 21:
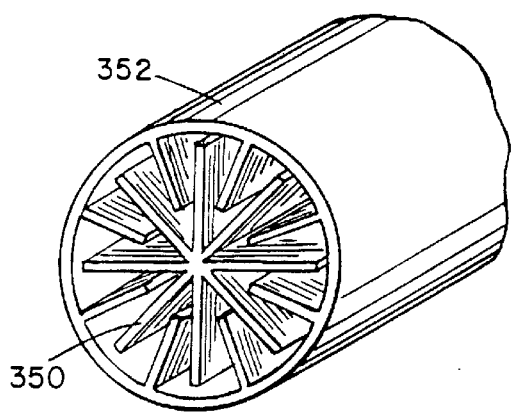
FIG. 21 is a perspective view of one end of an alternative, finned conductor structure of the sensor.
Figure 22:
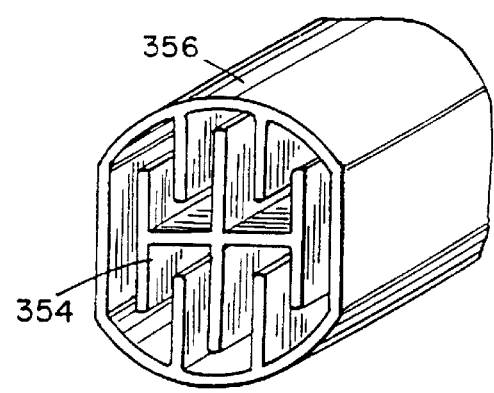
FIG. 22 is a perspective view of one end of another alternative, finned conductor structure of the sensor.
Figure 23:
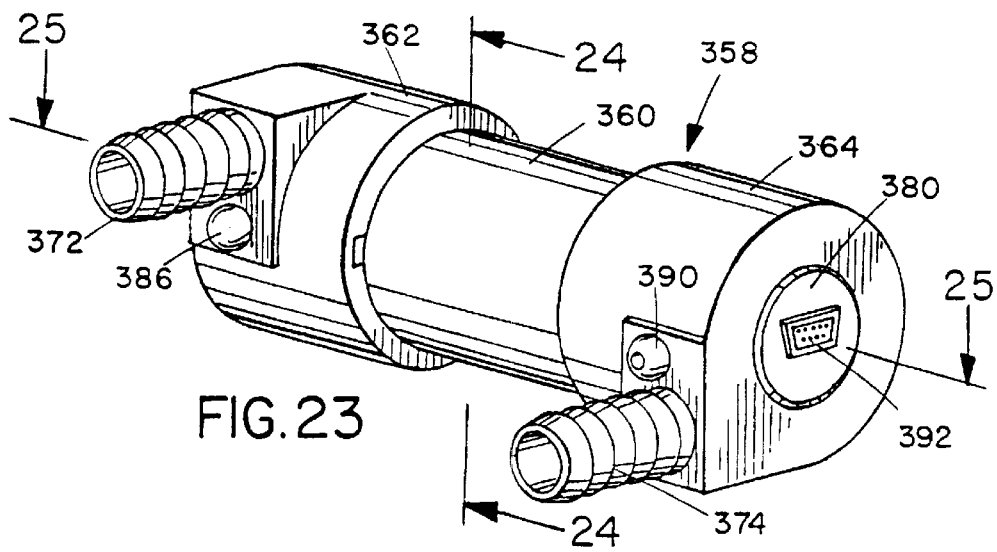
FIG. 23 is a perspective view of an alternative sensor having a concentric tubular conductor arrangement.
Figure 24:
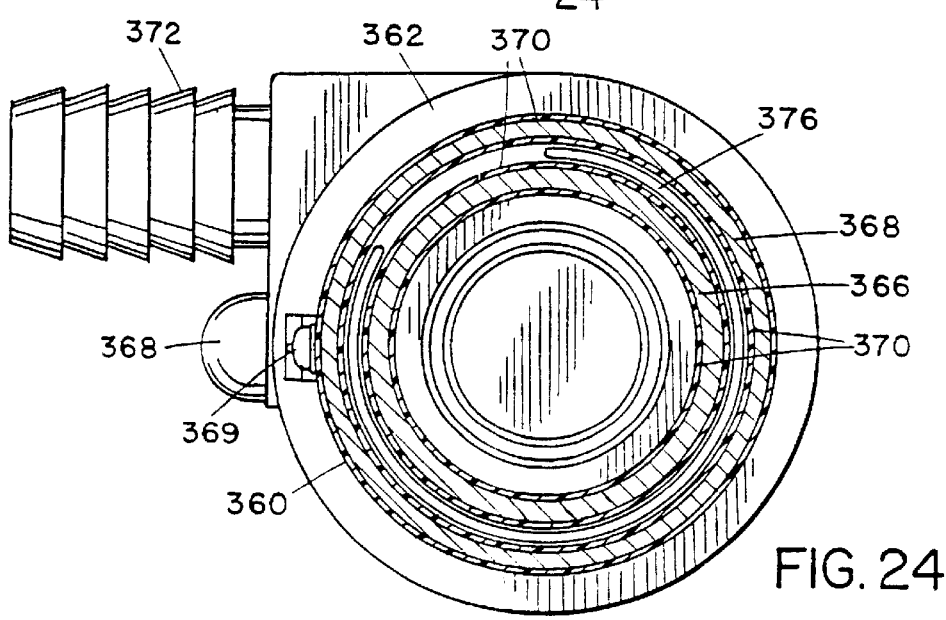
FIG. 24 is an enlarged sectional view taken on line 24—24 of FIG. 23.
Figure 28:
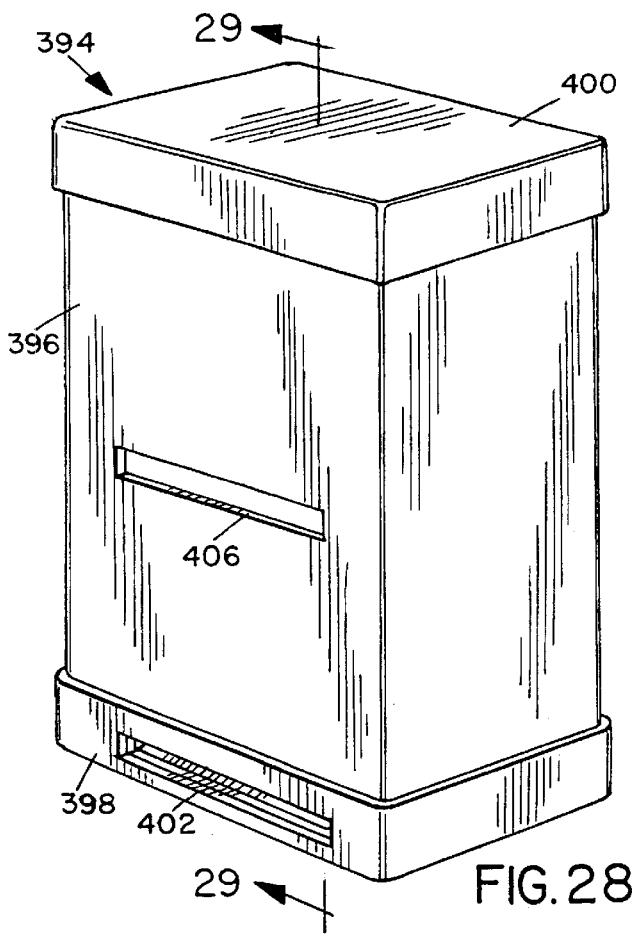
FIG. 28 is a perspective view of an alternative, immersible sensor.
Figure 29:
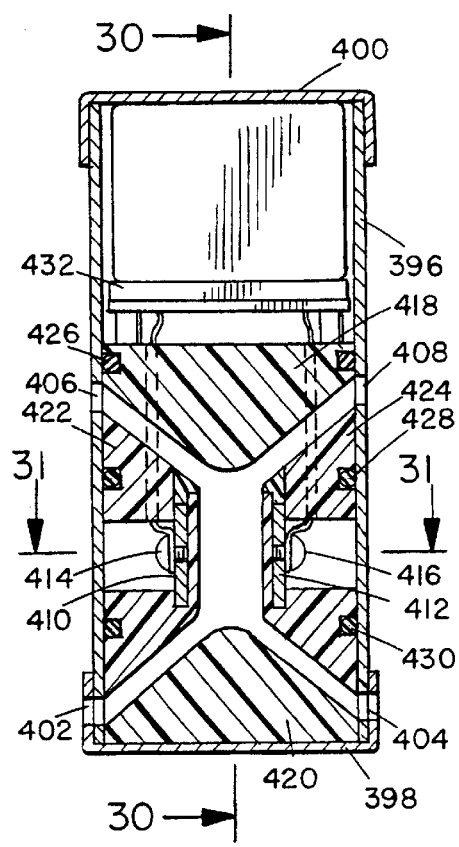
FIG. 29 is a sectional view taken on line 29—29 of FIG. 28.
Figure 30:
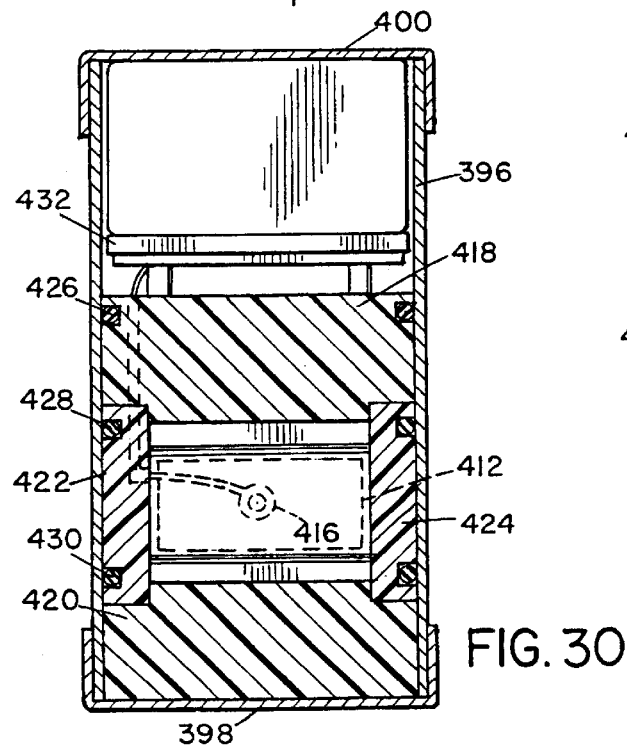
FIG. 30 is a sectional view taken on line 30—30 of FIG. 29.
Figure 31:
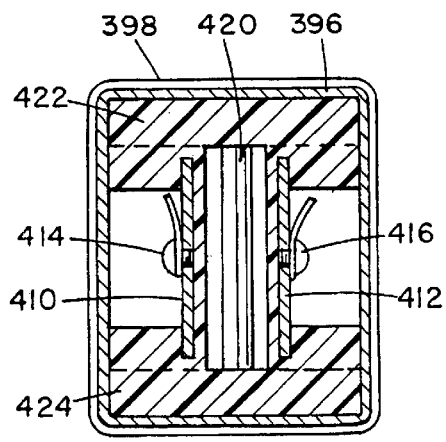
FIG. 31 is a sectional view taken on line 31—31 of FIG. 29.

As illustrated in FIG. 21, a sensor of the general type illustrated in FIGS. 15–20 may have an alternative conductor assembly that includes an inner conductor 350 with radial fins concentrically disposed within an outer, cylindrical conductor 352 with radial fins that mesh with those of conductor 350. The large surface area of the fins provides a greater capacitance in response to a given charge density than embodiments having two bar-like conductors or two concentric cylindrical conductors. The fins may be arranged in any suitable geometry, as illustrated by FIG. 22, in which the fins of the inner conductor 354 have an "H"-like shape and mesh with the fins of an outer conductor 356.

As illustrated in FIGS. 23–27, another alternative capacitive sensor 358 includes an elongated, generally tubular electrically conductive body 360 and two endpieces 362 and 364 that together function as shield against external electric fields. Enclosed inside and thus protected against the effects of such fields are an inner cylindrical conductor 366 disposed concentrically within an outer cylindrical conductor 368. Contact screws 367 and 369 connect electrical wires to conductors 366 and 368. Conductors 366 and 368 are coated with a suitable dielectric coating 370 to prevent electrical conduction between them through the fluid (not shown). The space between conductors 366 and 368 defines the chamber in which the material sample is measured. Ports 372 and 374 are retained in endpieces 362 and 364, respectively, and allow fluid to flow through sensor 358. They are arranged with their directions of flow perpendicular to the longitudinal axis of sensor 358 to minimize the area of conductors 366 and 368 exposed to external electric fields entering through ports 372 and 374. Each of endpieces 362 and 364 has a spiral, slot-like groove 376 that communicates the fluid between each of ports 372 and 374 and the chamber. The spiral shape promotes smooth flow into and out of sensor 358 and eliminates sites at which bubbles could accumulate, thereby enhancing measurement accuracy.

As illustrated in FIG. 25, the sensor electronics 378 are enclosed within sensor 358. As noted above with regard to other embodiments, enclosing the sensor electronics within the conductors and/or within an outer shield protects the electronics against the adverse effects of external electric fields. Two endcaps 380 and 382 seal endpieces 362 and 364 following assembly of electronics 378 inside sensor 358. Electronics 378 may comprise any of the circuitry described above, or any of the alternative circuitry described below. In this embodiment, a light-emitting diode (LED) indicator 384 is provided to indicate the output measurement. As described below, such an indicator may be used to provide a "GO-NOGO" indication; i.e., whether the measurement of the material sample is above or below some predetermined threshold. Such a binary indicator is a suitable alternative indicator to the digital display type of indicator described with regard to certain other embodiments. LED indicator 384 fits within a plug 386 in one of endpieces 362 and 364. An electrical cable 388 carrying signals to external electronics, such as a digital display (not shown), exits sensor 358 through a similar plug 390 in the other endpiece. A multiple-pin connector 392 fits within an opening in endcap 380 and provides signals for external data acquisition devices or test equipment (not shown).

As illustrated in FIGS. 28–31, still another alternative capacitive sensor 394 includes an elongated, generally rectangular body 396 that is made of a conductive material and thus functions as an outer shield against electric fields. Conductive endpieces 398 and 400 seal body 396 and thus form part of the shield. Sensor 394 has a configuration that facilitates measurement of a fluid by immersing it in the fluid (not shown). Slot-like ports 402 and 404 at one end of body 396 and slot-like ports 406 and 408 at the opposite end of body 396 allow fluid to flow into and out of the measurement chamber, which is defined by the space between two plate-shaped conductors 410 and 412. Contact screws 414 and 416 connect electrical wires to conductors 410 and 412. Forms 418, 420, 422 and 424, which are made of a non-conductive material, allow the fluid to flow freely into and out of the chamber and between ports 402, 404, 406 and 408. Elastomeric gaskets 426, 428 and 430 provide seals between forms 418, 420, 422, 424, and body 396. When sensor 394 is immersed, the fluid flows into ports 402 and 404 and rises inside the chamber as sensor 394 is further immersed. The displaced air exits through ports 406 and 408. When fully immersed, the fluid covers all of ports 402–408 and completely fills the chamber. It should be noted that ports 402–408 are oriented with their directions of flow perpendicular to the longitudinal axis of sensor 394 so that external electric fields entering through them are not directed at conductors 410 and 412. An advantage of this arrangement is that air bubbles are not entrapped in the chamber and can escape through ports 406 and 408.

As in other embodiments described above, sensor 394 includes electronics 432 that are also enclosed within the shield defined by body 396 and endpieces 398 and 400. Although not shown for purposes of clarity sensor 394 may have a suitable indicator, such as a digital display or LED indicator, and may in addition, or alternatively, have a cable that provides electrical connections between electronics 432 and external circuitry, as in other embodiments described above.

Figure 36:
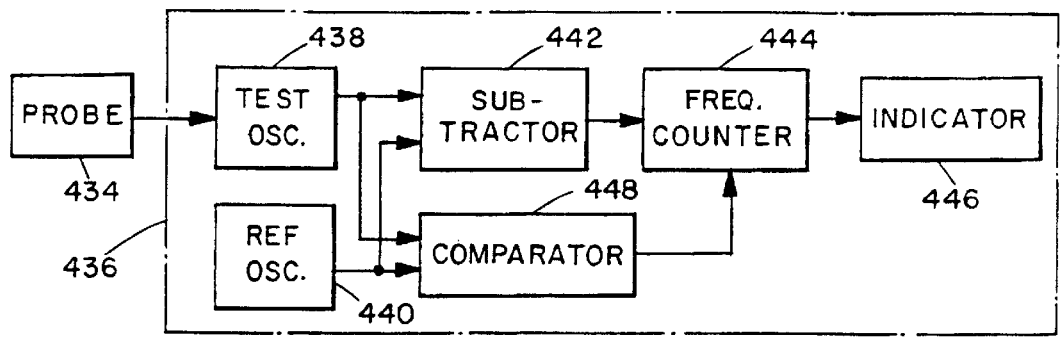
FIG. 36 is a block diagram of a sensing system that subtracts a measured test frequency from a predetermined reference frequency.

FIG. 36 is a generalized block diagram illustrating a system as described above, and comprises a sensor 434 and electronics 436. Sensor 434 may be any of those described above or any other suitable capacitive sensor. As described above with regard to the schematic diagrams of FIGS. 11–14, a test oscillator 438 produces a signal having a frequency responsive to the impedance of sensor 434. A reference oscillator 440 produces a signal having a predetermined reference frequency. A subtractor circuit 442 subtracts the test frequency signal from the reference frequency signal. A frequency counter circuit 444 produces an indication signal in response to the difference between these frequencies. The indication signal is output in a suitable user-perceptible manner by an indicator 446, such as a digital display, one or more LEDs, an audio transducer, or any other suitable device. A comparator circuit 448, such as described above with regard to FIGS. 11–14, compares the test frequency signal to the reference frequency signal, and if the reference frequency exceeds the test frequency, it forces frequency counter circuit 444 to zero. Such a condition may occur if, for example, only air is present in the measurement chamber of sensor 434.

Figure 37:
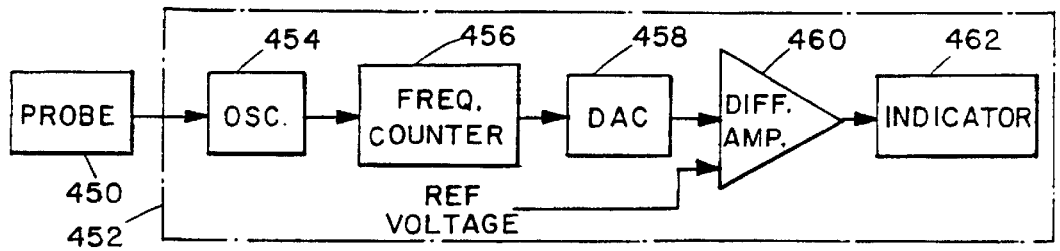
FIG. 37 is a block diagram of an alternative sensing system that includes a differential amplifier.

FIG. 37 is a generalized block diagram of an alternative system that includes a sensor 450 and electronics 452. Electronics 452 include an oscillator circuit 454 that produces a signal having a frequency responsive to the impedance of sensor 450, a frequency counter circuit 456 that produces a digital signal responsive to oscillator circuit 454, a digital-to-analog converter (DAC) 458 that converts the digital signal to analog, a differential amplifier 460 that produces a signal responsive to the difference between the converted signal and a reference voltage, and an indicator circuit 462. This system is similar to that illustrated in FIG. 36, but uses a differential amplifier circuit rather than a subtraction circuit to determine the difference between the test frequency and a reference value. Although not illustrated, a further alternative embodiment involves substituting a comparator for differential amplifier 460. A suitable indicator circuit 462, such as a LED circuit, would provide an indication if the measured value is above (or equivalently, below) a predetermined threshold corresponding to the reference voltage.

Figure 38:
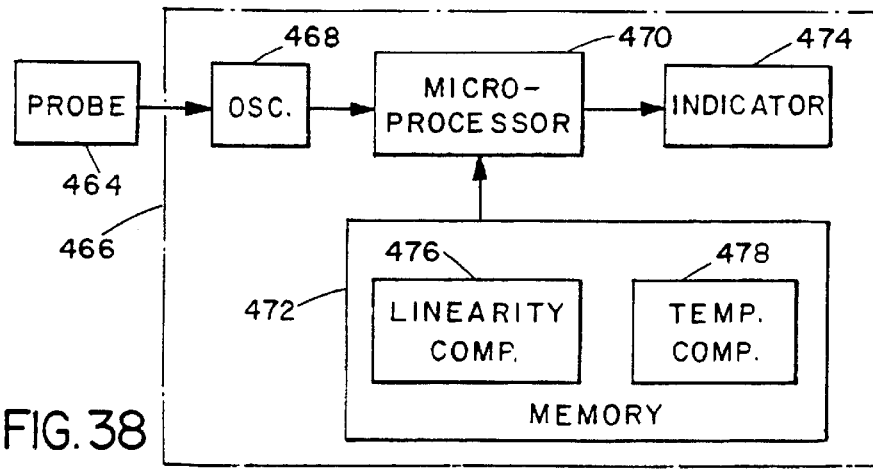
FIG. 38 is a block diagram of another alternative sensing system that includes a microprocessor and compensates for temperature effects and non-linearities.

The system can alternatively include digital electronics, as illustrated in FIG. 38. This alternative system includes a sensor 464 and electronics 466. Electronics 466 include an oscillator circuit 468 that produces a signal having a frequency responsive to the impedance of sensor 464, a microprocessor circuit 470, a memory 472, and an indicator circuit 474. The microprocessor is programmed in a suitable manner to count the frequency of the signal and output the result to indicator circuit 474. Scaling and other functions performed by analog circuitry in the embodiments described above can be performed by the microprocessor as well. The microprocessor can also compensate for any nonlinearity in the response of sensor 464 to changes in the volume charge density of the material sample by applying a suitable linearizing function 476, described in further detail below. Similarly, the microprocessor can compensate for undesirable variations in the measured quantity resulting from variations in environmental temperature by applying a suitable compensation function 478, as described in further detail below. Functions 476 and 478 are illustrated as residing in memory 472 for conceptual purposes only; persons skilled in the art will readily be capable of incorporating such functions into a suitable program.

Figure 32:
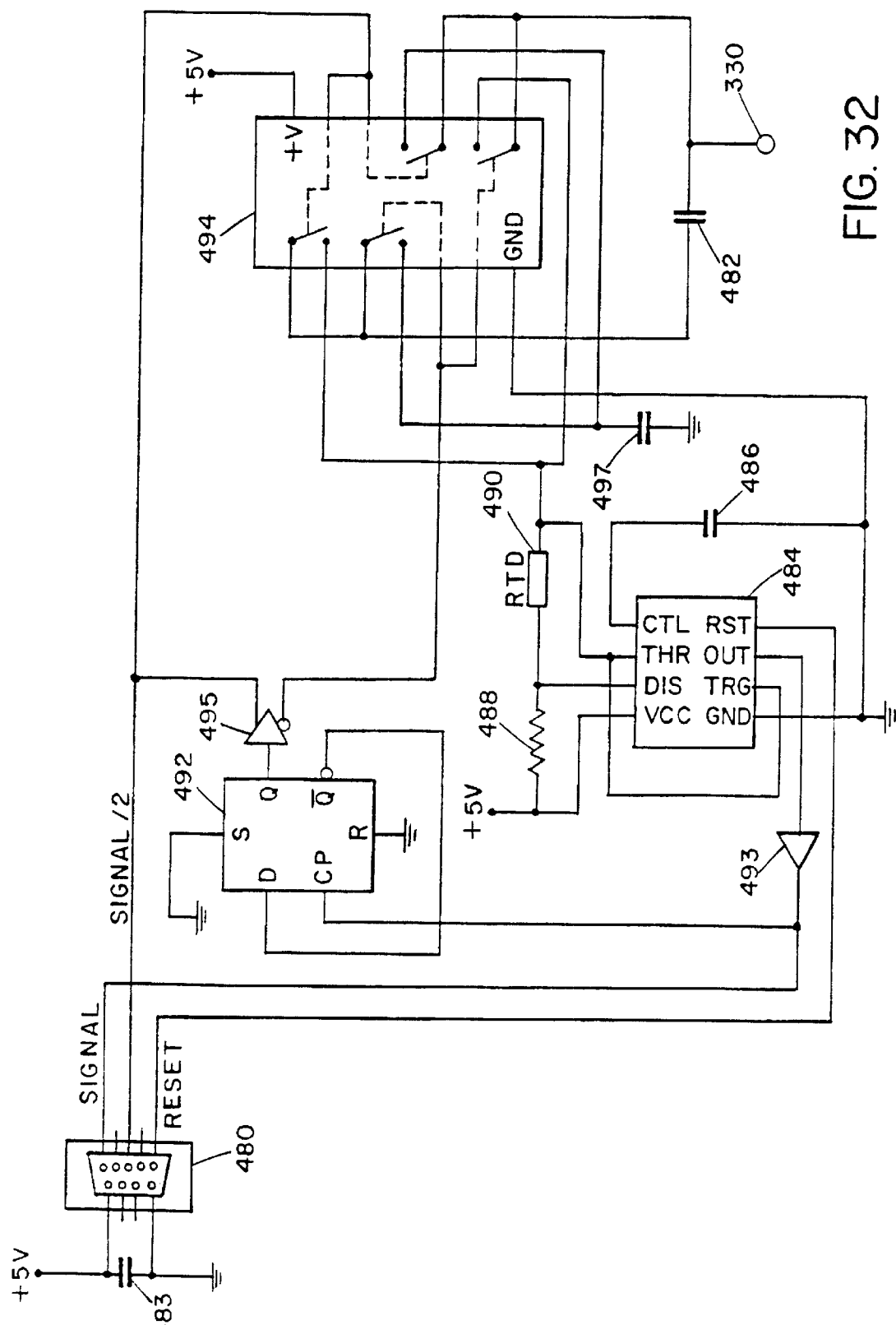
FIG. 32 is a schematic circuit diagram of a sensor portion of an alternative capacitive sensing circuit having a temperature-compensation circuit and a circuit that reverses the polarity of the sensor conductors with respect to the ground potential of a sensor shield.

FIGS. 32–35 and 43 illustrate some alternative embodiments of the electronics. FIG. 32 illustrates the portion of the circuit that directly interfaces with the sensor and is preferably enclosed within a shielded portion of the sensor, as described above. This portion of the circuit reverses the polarity of the signal applied to the sensor conductors with respect to a ground potential at which an outer sensor shield is held. A connector 480 interfaces the sensor with the remaining electronics, and may be, for example, connector 348 of the sensor embodiment illustrated in FIG. 15 or connector 392 of the sensor embodiment illustrated in FIG. 25. A capacitor 482 represents the sensor capacitance, i.e., the capacitance defined by the two conductors and the dielectric material sample and any other dielectric elements between them. Power (+5V and ground) is also provided to the sensor via connector 480. A filter capacitor 483 is coupled between the supply signal (+5V) and ground.

As described above with regard to the sensor embodiment illustrated in FIG. 17, screw 330 may be coupled to one of the conductors to enhance the resolution of the sensor. Alternatively, screw 330 may be coupled to chassis ground, i.e., earth ground, and the conductive case or body of the sensor to promote noise reduction. Note that chassis ground or earth ground is not directly tied to the digital ground of the illustrated circuitry, in accordance with conventional engineering practices. Screw 330 is preferably a gold-plated screw of the rolled-thread type, which resists wearing of the plating.

A 555-type timer chip 484 is configured as a free-running oscillator by coupling its TRIGGER and THRESHOLD pins together, coupling a capacitor 486 between its CONTROL pin and ground, and coupling a resistor 488 between its DISCHARGE pin and the supply voltage (VCC). A RTD resistor 490, the resistance of which changes in response to temperature, is coupled between the DISCHARGE and THRESHOLD pins to compensate for undesirable variations in the measured quantity resulting from variations in environmental temperature. The clock input (CP) of a D-type flip-flop 492 is coupled to the OUTPUT pin of timer chip 484 via a non-inverting buffer 493 and divides the frequency of this signal by two. Both the signal and the signal divided by two are provided to pins of connector 480, the latter being provided via the non-inverted output of a buffer 495. Via the inverted output of buffer 495, the complement of signal divided by two is also provided to an electronically controlled switch chip 494. On one cycle of this slower signal, chip 494 couples one of the conductors (plates of capacitor 482) to ground, and on the next cycle couples the other conductor to ground. This action prevents the undesirable buildup of charge on either one of the conductors by alternately discharging them to ground. A ground isolation capacitor 497 isolates the sensor from the circuitry at low frequencies.

Figure 33:
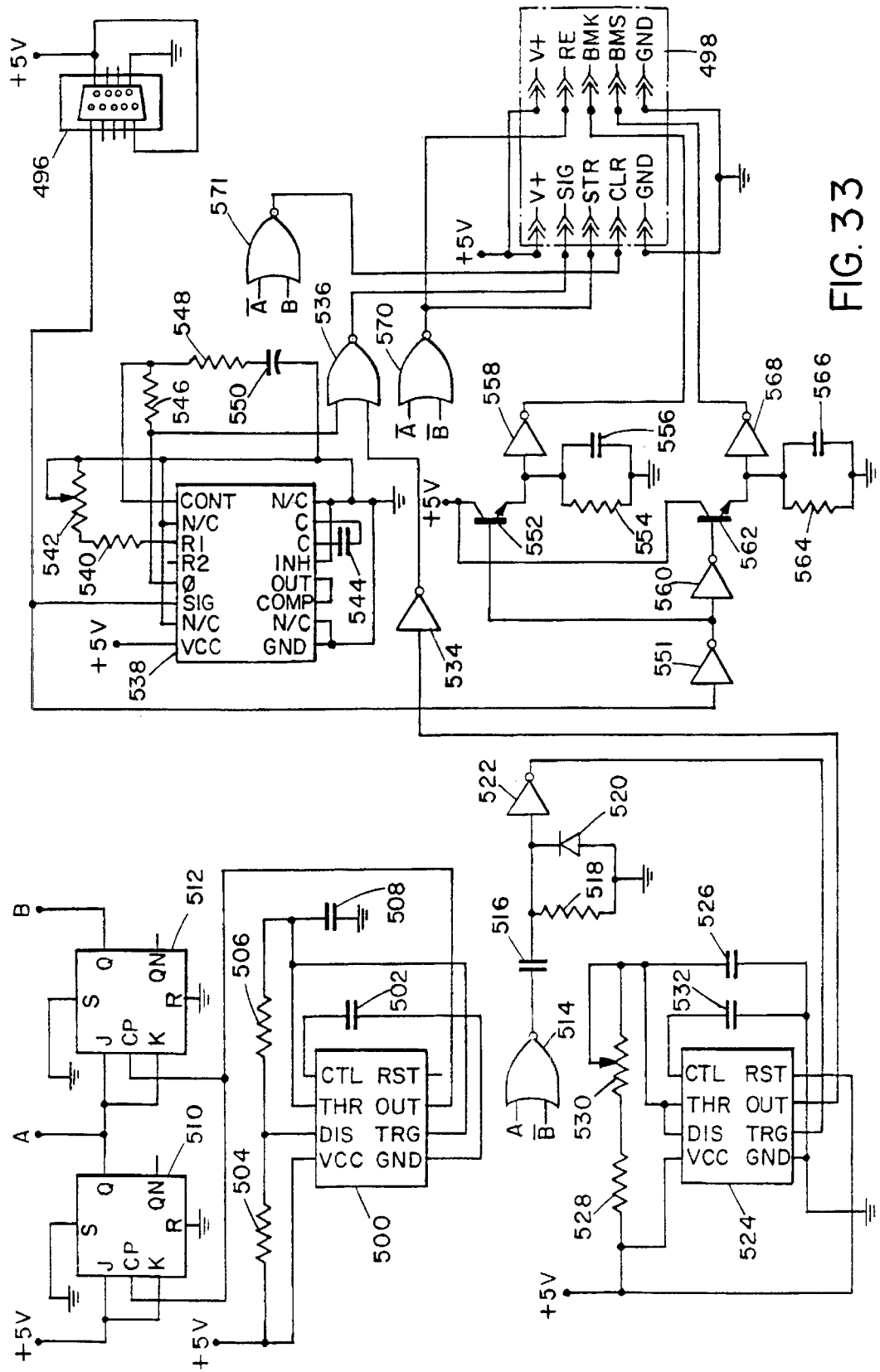
FIG. 33 is a schematic circuit diagram of the instrument portion of the alternative capacitive sensing circuit.

Connector 480 of the sensor may be coupled to a mating connector 496 of another portion of the electronics, illustrated in FIG. 33. This portion of the electronics in turn interfaces via a connector 498 with a suitable digital display indicator circuit, such as that illustrated in FIG. 13 and described above.

Figure 43:
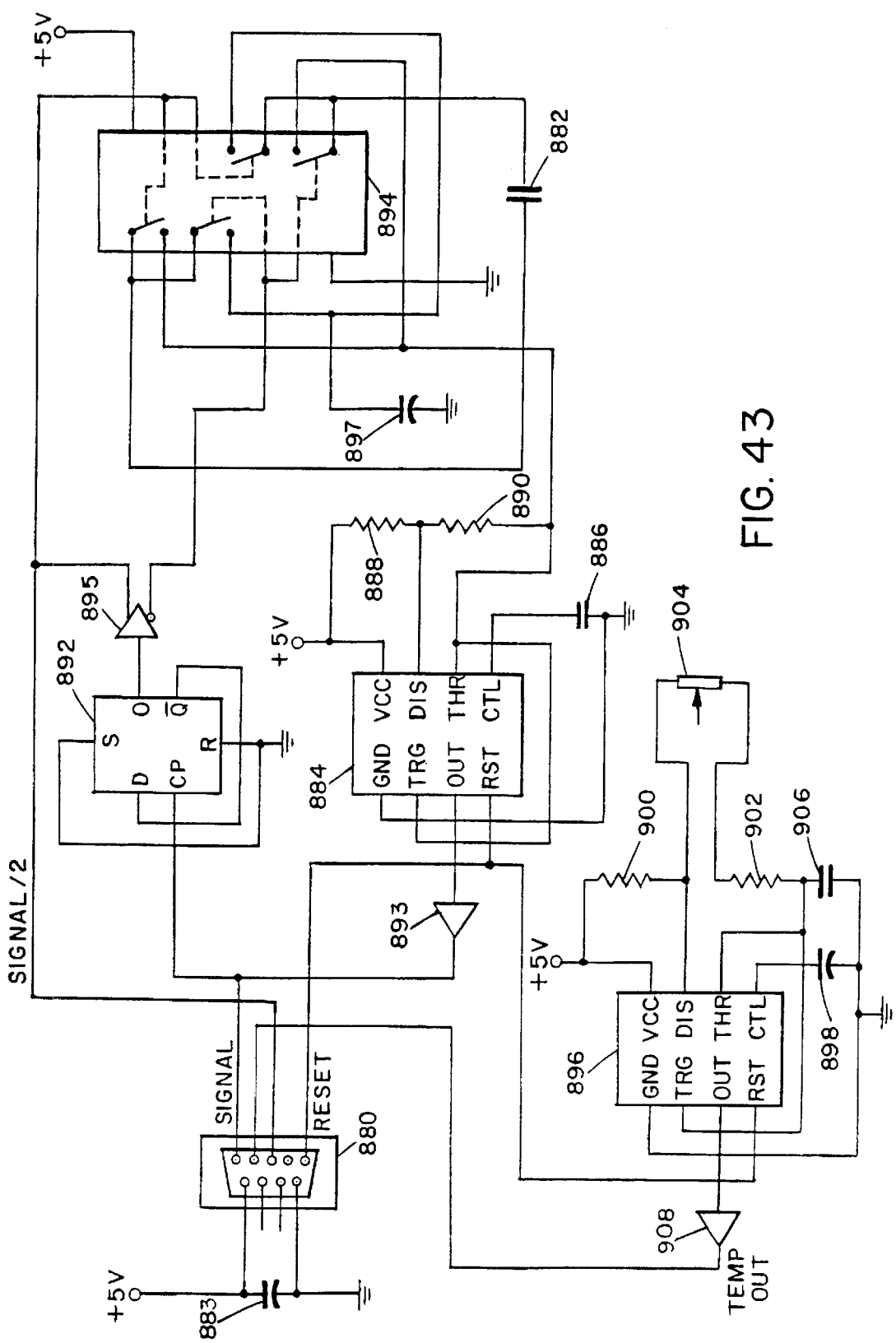
FIG. 43 is a schematic circuit diagram of the sensor portion of another alternative capacitive sensing circuit having an alternative temperature-compensation circuit.
Figure 44:
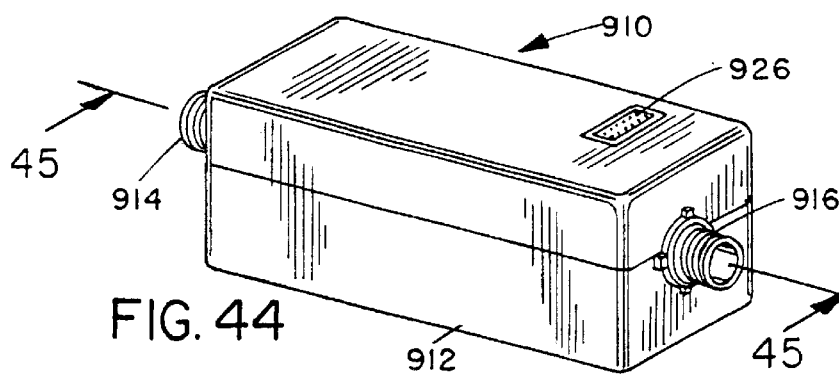
FIG. 44 is a perspective view of another alternative sensor having a parallel plate-like conductor arrangement.
Figure 45:
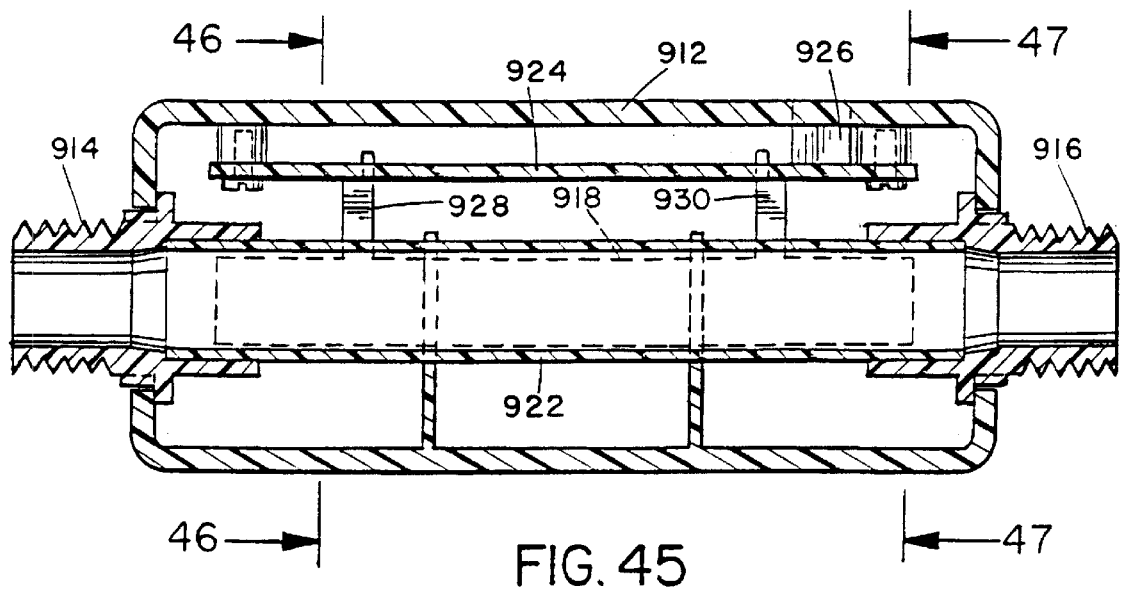
FIG. 45 is an enlarged sectional view taken on line 45—45 of FIG. 44.
Figure 46:
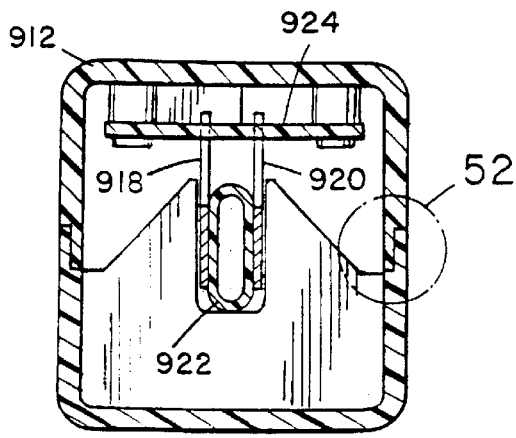
FIG. 46 is a sectional view taken on line 46—46 of FIG. 45.
Figure 47:
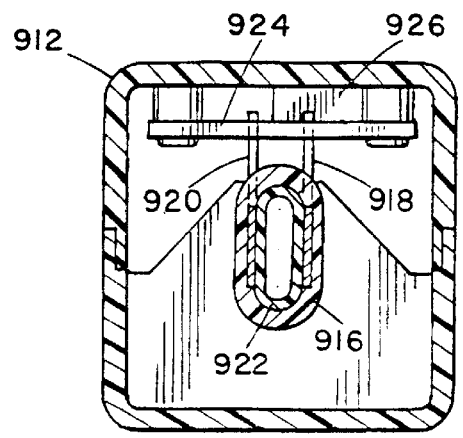
FIG. 47 is a sectional view taken on line 47—47 of FIG. 45.
Figure 48:
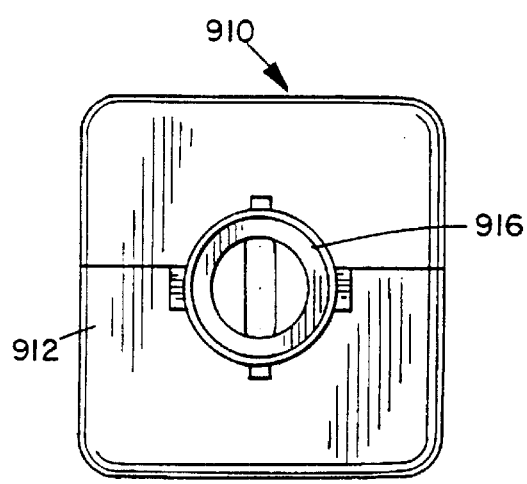
FIG. 48 is an end view of the sensor of FIG. 45.
Figure 49:
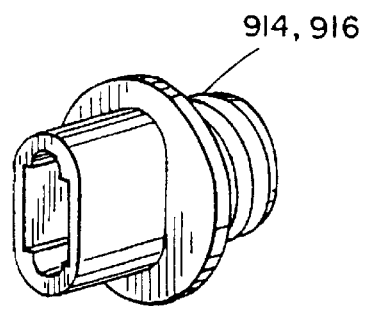
FIG. 49 is a perspective view of one side of the endpiece of the sensor of FIG. 44.
Figure 50:
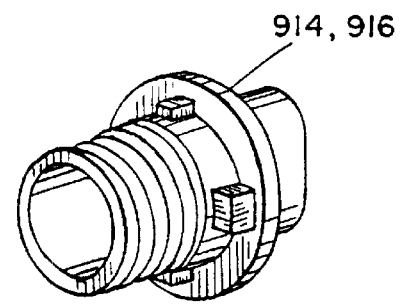
FIG. 50 is a perspective view of the opposite side of the endpiece of FIG. 49.
Figure 51:
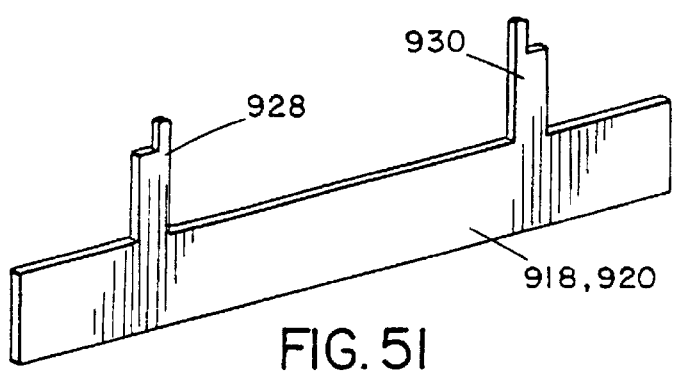
FIG. 51 is a perspective view of the plate-like or bar-like conductor of FIG. 44.
Figure 52:
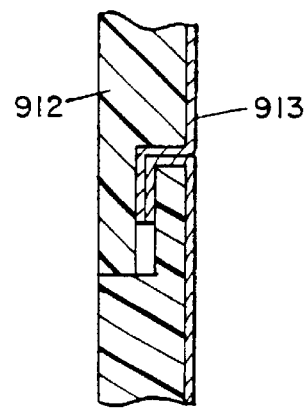
FIG. 52 is an enlargement of the encircled portion of FIG. 46.

FIG. 43 is an embodiment of the sensor interface circuitry similar to that of FIG. 32, but which uses a thermistor rather than a RTD resistor to provide temperature-compensation. As in FIG. 32, a connector 880 interfaces the sensor with the remaining electronics. A capacitor 882 represents the sensor capacitance. A filter capacitor 883 is coupled between the supply signal (+5V) and ground. A 555-type timer chip 884 is configured as a free-running oscillator by coupling its TRIGGER and THRESHOLD pins together, coupling a capacitor 886 between its CONTROL pin and ground, and coupling a resistor 888 between its DISCHARGE pin and the supply voltage (VCC), and coupling another resistor 890 between the DISCHARGE and THRESHOLD pins. The clock input (CP) of a D-type flip-flop 892 is coupled to the OUTPUT pin of timer chip 884 via a non-inverting buffer 893 and divides the frequency of this signal by two. Both the signal and the signal divided by two are provided to pins of connector 880, the latter being provided via the non-inverted output of a buffer 895. Via the inverted output of buffer 895, the complement of signal divided by two is also provided to an electronically controlled switch chip 894. As in the embodiment described above with respect to FIG. 32, on one cycle of this slower signal, chip 894 couples one of the conductors (plates of capacitor 882) to ground, and on the next cycle couples the other conductor to ground. This action prevents the undesirable buildup of charge on either one of the conductors by alternately discharging them to ground. A ground isolation capacitor 897 isolates the sensor from the circuitry at low frequencies.

Unlike the circuit of FIG. 32, this circuit further includes another 555-type timer chip 896, which is configured as a free-running oscillator by coupling its TRIGGER and THRESHOLD pins together, coupling a capacitor 898 between its CONTROL pin and ground, coupling a resistor 900 between its DISCHARGE pin and the supply voltage (VCC), and coupling another resistor 902 in series with a thermistor 904 between the DISCHARGE and THRESHOLD pins. A capacitor 906 is coupled between the THRESHOLD pin and ground. In operation, this circuit provides a signal ("TEMP OUT") to connector 880 via a non-inverting buffer 908. This signal has a frequency that varies in response to the ambient temperature and can be used by the sensor to compensate for temperature.

As an alternative to the use of the described oscillator to provide the frequency signal for temperature compensation, an A/D converter can be used to track the changes in voltage output of the thermistor. Using the clock pulse the A/D converter generates a digital output to the microprocessor that varies with ambient temperature and can be used to compensate for temperature variations. Design of such A/D converter circuits, e.g., tracking or servo AND converter circuits, are well known to those of skill in the art.

With reference to FIG. 33, a 555-type timer chip 500 is configured as a free-running oscillator by coupling its TRIGGER and THRESHOLD pins together, coupling a capacitor 502 between its CONTROL pin and ground, coupling a first resistor 504 between its DISCHARGE pin and the supply voltage (VCC), and coupling a second resistor 506 between its DISCHARGE pin and ground, via a capacitor 508. The output (OUT) pin of chip 500 is coupled to the clock (CP) inputs of two JK-type flip-flops 510 and 512. The J and K inputs of flip-flop 510 are tied to the supply voltage, and the output (Q) is coupled to the J and K inputs of flip-flop 512. The outputs (Q) of flip-flops 510 and 512 provide timing signals A and B, respectively, to other circuit elements, as described below.

Figure 40:
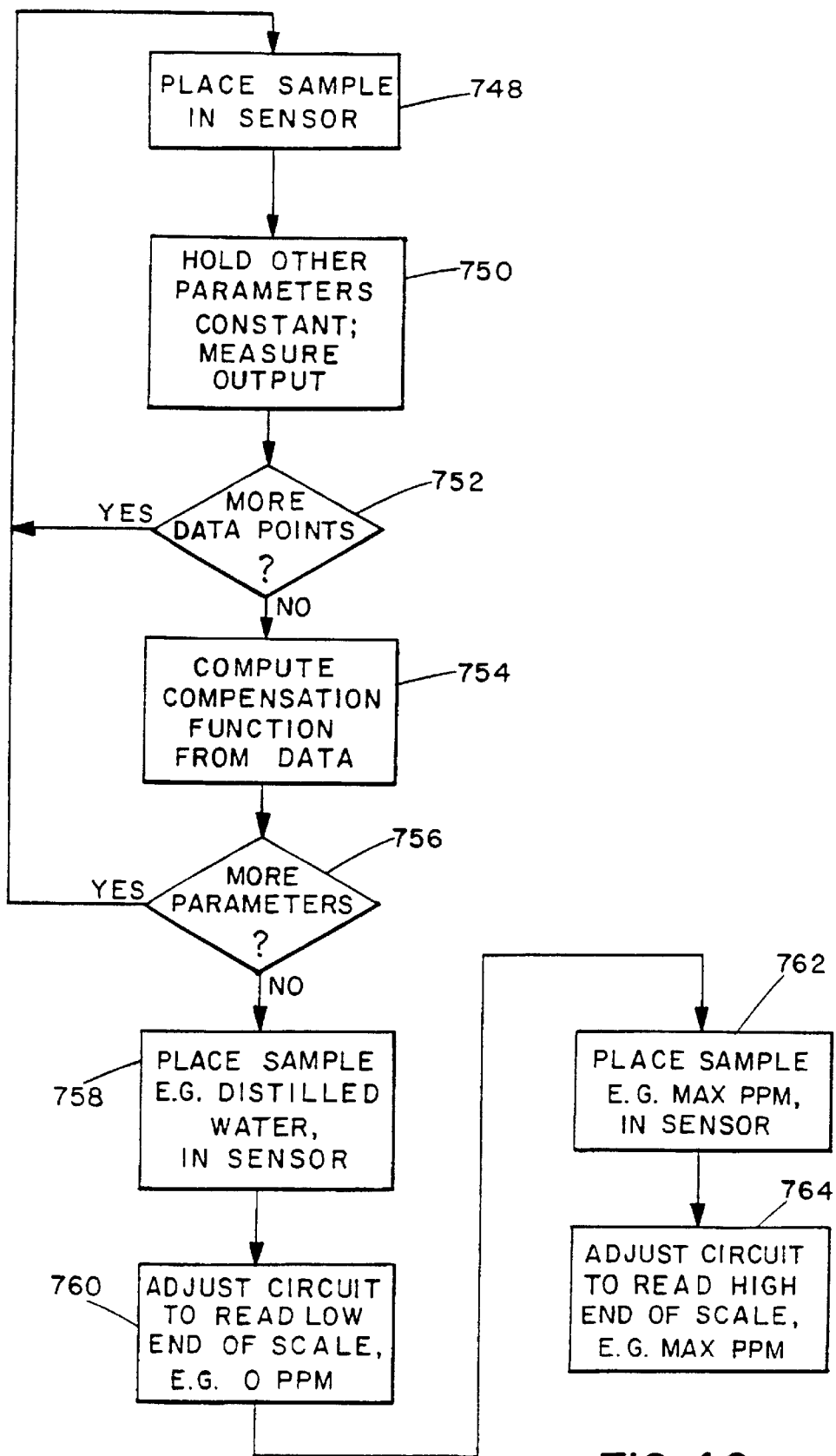
FIG. 40 is a flow diagram illustrating a method for calibrating the system.

When signal A is low and signal B is high, a NOR gate 514 triggers a pulse generator circuit comprising a capacitor 516 and a resistor 518. The resulting pulse is detected by an edge detector circuit comprising a diode 520 and an inverter 522. The detected signal is used to trigger the generation of a delay signal that inhibits the main clock during the measurement interval and is thus similar to signal 171 discussed above with regard to the embodiment illustrated in FIG. 11. Indeed, a 555-type timer chip 524 is configured as a monostable multivibrator or one-shot in the same manner as chip 188 (FIG. 11). That is, one terminal of a capacitor 526 is coupled to the THRESHOLD and TRIGGER inputs, and the other terminal is coupled to ground. Two resistors 528 and 530 are connected in series with one another between the first terminal of capacitor 526 and the DISCHARGE and THRESHOLD inputs of chip 524. Resistor 530 is a variable resistor that facilitates the calibration procedure mentioned above and described in further detail below with regard to FIG. 40. A capacitor 532 is connected between the CONTROL input of chip 524 and ground.

The OUTPUT signal of chip 524 is provided via an inverter 534 to a NOR gate 536. The output of gate 536 is coupled a SIG pin of connector 498. While this signal remains high, gate 536 holds the SIG pin low, thereby inhibiting the output frequency of the subtractor circuit from reaching the display circuit. While the signal is low, however, gate 536 passes to the display circuit the difference signal that represents the measured quantity.

A 4046-type phase-locked loop chip 538 generates the difference signal. The oscillator frequency of chip 538 is determined by two resistors 540 and 542 coupled between a designated pin (R1) and ground, and a capacitor 544 coupled between two designated pins (C). Resistor 542 is a variable resistor that facilitates calibration in the a manner similar to adjusting the reference signal frequency described above with regard to the embodiment illustrated in FIG. 11. The control pin (CONT) is coupled via a resistor 546 to the phase error ($\phi$) pin as well as coupled via a resistor 548 and a capacitor 550 to ground. The output (OUT) and compare (COMP) pins are coupled together. The measurement signal produced by the sensor is available at connector 496, which is coupled to the signal (SIG) pin. The phase error pin is also coupled to the other input of NOR gate 536 and thus represents the difference between the oscillator frequency of chip 538 and the frequency of the measurement signal produced by the sensor.

The remaining portion of the circuit relates to providing error indications and receives the measurement signal via an inverter 551. If the sensor malfunctions, the measurement signal will have a zero frequency and thus remain in either a high or low logic state. If the measurement signal remains high, a circuit comprising a transistor 552, a resistor 554, a capacitor 556 and an inverter 558 cause the BMK pin of connector 498 to go high. If the measurement signal remains low, a circuit comprising an inverter 560, a transistor 562, a resistor 564, a capacitor 566 and another inverter 568 cause the BMS pin of connector 498 to go high.

As noted above, the display circuit is not shown for purposes of clarity. Nevertheless, the circuit illustrated in FIG. 33 includes a NOR gate 570 for providing a strobe signal via a STR pin of connector 498 in response to a combination of signals A and B. The display circuitry uses the strobe signal as described above with respect to strobe signal 234 of FIG. 13. Similarly, when signal A is low and B is high, a NOR gate 571 provides a signal to clear the display via CLR pin of connector 498.

Figure 34:
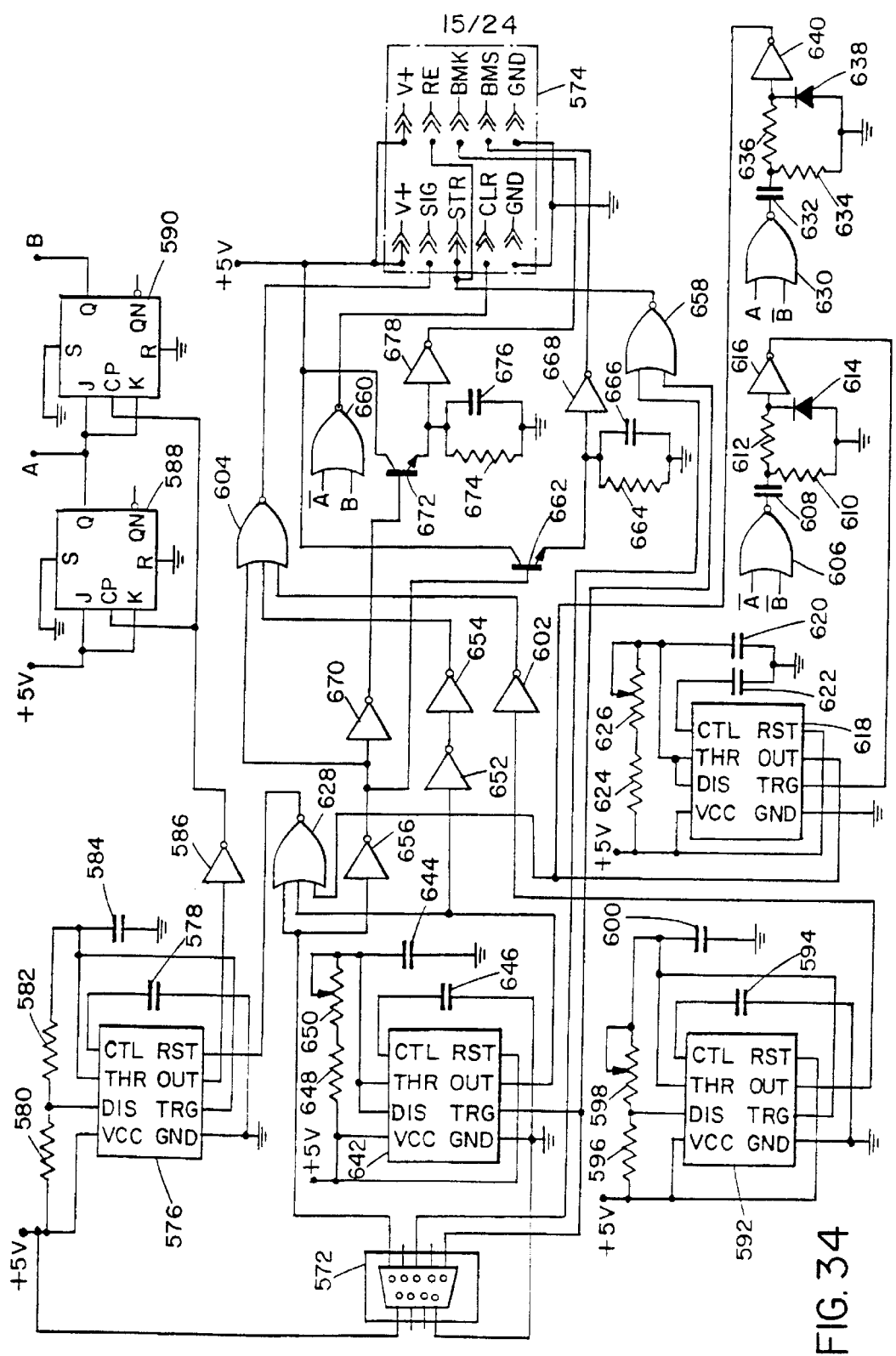
FIG. 34 is a schematic circuit diagram of an alternative instrument portion of the capacitive sensing circuit.

FIG. 34 illustrates an alternative to the circuit illustrated in FIG. 33. In this circuit, the output signal sent to the display circuit has a frequency that is directly proportional to the time constant of a flip-flop configured as a one-shot, but is gated to provide that frequency for an interval proportional to the frequency of the measurement signal received from the sensor circuit. The measurement or test signal is received from the sensor via a connector 572. The circuit interfaces with a display circuit such as that illustrated in FIG. 13 via a connector 574.

A 555-type timer chip 576 is configured as a free-running oscillator by coupling its TRIGGER and THRESHOLD pins together, coupling a capacitor 578 between its CONTROL pin and ground, coupling a first resistor 580 between its DISCHARGE pin and the supply voltage (VCC), and coupling a second resistor 582 between its DISCHARGE pin and ground, via a capacitor 584. The RESET pin of chip 576 is controlled by a signal described below such that the oscillation frequency is zero during the measurement period. The output (OUT) pin of chip 576 is coupled via an inverter 586 to the clock (CP) inputs of two JK-type flip-flops 588 and 590 The J and K inputs of flip-flop 578 are tied to the supply voltage, and the output (Q) is coupled to the J and K inputs of flip-flop 590 The outputs (Q) of flip-flops 588 and 590 provide timing signals A and B, respectively, to other circuit elements.

Another 555-type timer chip 592 is similarly configured as a free-running oscillator to generate a master clock signal having a frequency that is relatively high in comparison to the frequency of the measurement signal produced by the sensor. Its TRIGGER and THRESHOLD pins are coupled together, and a capacitor 594 is coupled between its CONTROL pin and ground. A first resistor 596 is coupled between its DISCHARGE pin and the supply voltage (VCC), and a second resistor 598 is coupled between its DISCHARGE pin and ground via a capacitor 600. The output (OUT) pin of chip 592 is a high frequency clock signal that is coupled via an inverter to one input of a three-input NOR gate 604. The output of NOR gate 604 is the difference signal representing the measured quantity, and is provided to the display circuitry via a SIG pin of connector 574.

When signals A and B are both low, a NOR gate 606 triggers a pulse generator circuit comprising a capacitor 608 and resistors 610 and 612. The resulting pulse is detected by an edge detector circuit comprising a diode 614 and an inverter 616. The detected signal is used to trigger the generation of a delay signal that inhibits the main clock during the measurement interval in a manner similar to that described above with respect to other circuit embodiments. A 555-type timer chip 618 is configured as a monostable multivibrator or one-shot. The THRESHOLD and DISCHARGE pins are coupled together. One terminal of a capacitor 620 is coupled to the THRESHOLD and DISCHARGE pins, and the other terminal is coupled to ground. One terminal of another capacitor 622 is coupled to the CONTROL input, and the other terminal is coupled to ground. Two resistors 624 and 626 are coupled in series between the supply voltage (VCC) and the DISCHARGE and THRESHOLD pins. Resistor 626 is a variable resistor that facilitates the calibration procedure. The output pin of chip 618 is coupled to one input of the three-input NOR gate 628 that disables timer chip 576 via its RESET pin.

The measurement interval is triggered when a NOR gate 630 detects that signal A is high and signal B is low. The output of NOR gate 630 is coupled to a pulse generator circuit comprising a capacitor 632 and resistors 634 and 636. The resulting pulse is detected by an edge detector circuit comprising a diode 638 and an inverter 640. The detected signal is coupled to the same input of NOR gate 628 to which the output of chip 618 is coupled.

Yet another 555-type timer chip 642 is configured as a one-shot. The THRESHOLD and DISCHARGE pins are coupled together. One terminal of a capacitor 644 is coupled to the THRESHOLD and DISCHARGE pins, and the other terminal is coupled to ground. One terminal of another capacitor 646 is coupled to the CONTROL input, and the other terminal is coupled to ground. Two resistors 648 and 650 are coupled in series between the supply voltage (VCC) and the DISCHARGE and THRESHOLD pins. Resistor 650 is a variable resistor that facilitates the calibration procedure. The output pin of chip 642 is coupled to the second input of NOR gate 628 as well as to the second input of NOR gate 604 via two inverters 652 and 654.

The third input of NOR gate 628 is coupled to the pin of connector 572 that receives the measurement signal from the sensor. When the three signals received by NOR gate 628 are low, it produces a high output that enables timer chip 576 via its RESET pin. The measurement signal is also coupled to the third input of NOR gate 604 via an inverter 656.

A NOR gate 658 provides a clear signal to the display circuitry via a CLR pin of connector 574. Another NOR gate 660 provides a strobe signal via a STROBE pin of connector 574 when signal A is low and B is high.

The remaining portion of the circuit relate to providing error indications, as described above with respect to the embodiment illustrated in FIG. 33. If the measurement signal is stuck low, a circuit comprising a transistor 662, a resistor 664, a capacitor 666 and an inverter 668 cause the BMS pin of connector 574 to go high. If the measurement signal is stuck low, a circuit comprising an inverter 670, a transistor 672, a resistor 674, a capacitor 676 and another inverter 678 cause the BMK pin of connector 498 to go high.

Figure 35:
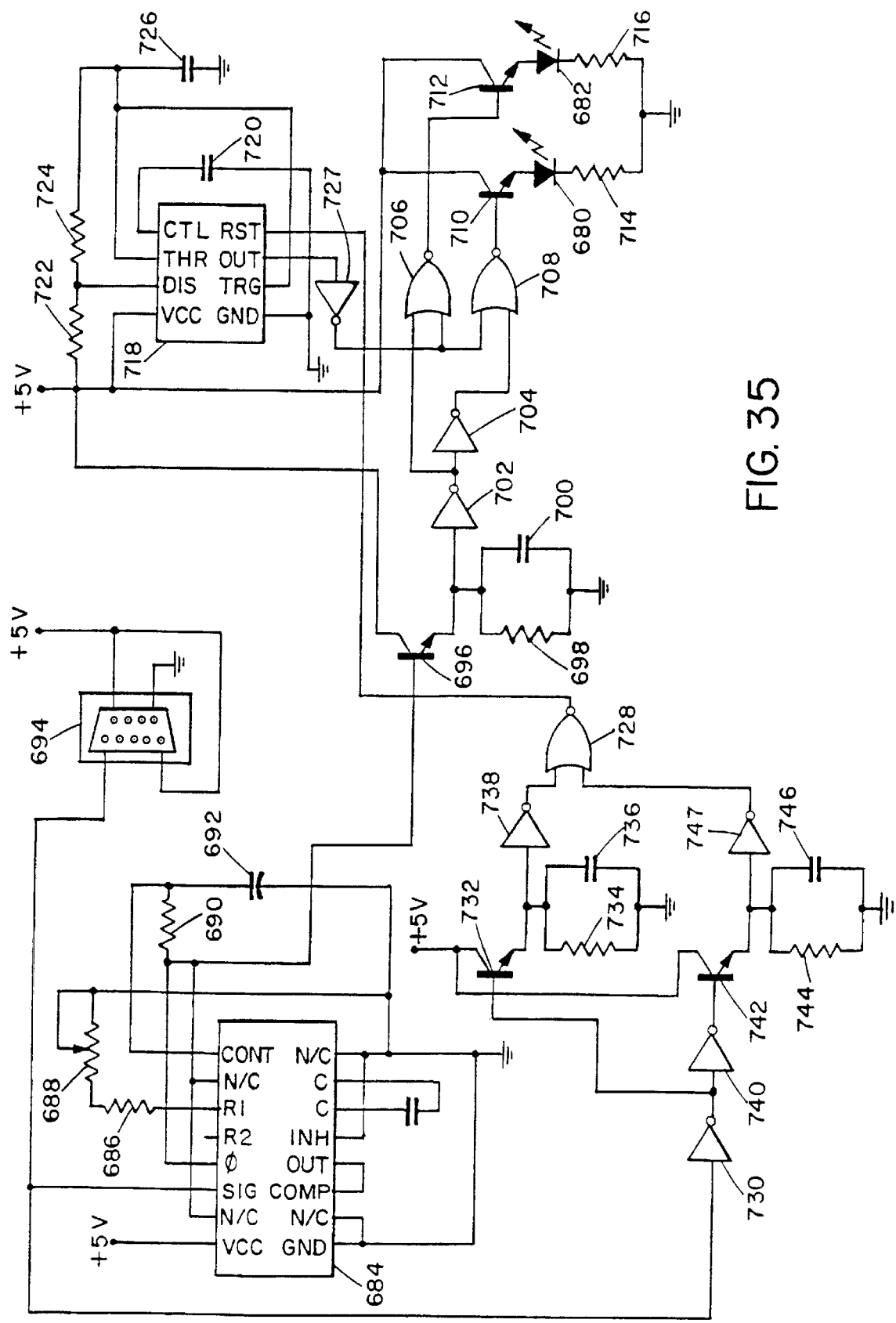
FIG. 35 is a schematic circuit diagram of an alternative instrument and indicator circuit portion of the capacitive sensing circuit that indicates whether the measurement is above or below a predetermined threshold.

FIG. 35 illustrates still another alternative circuit. In this embodiment, the indicator is not a digital display but rather consists of two light-emitting diodes (LEDs) 680 and 682. A 4046-type phase-locked loop chip 684 generates the difference signal. The oscillator frequency of chip 684 is determined by two resistors 686 and 688 coupled between a designated pin (R1) and ground, and a capacitor 544 coupled between two designated pins (C). Resistor 688 is a variable resistor that facilitates calibration. The control pin (CONT) is coupled via a resistor 690 to the phase error (φ) pin as well as coupled via a capacitor 692 to ground. The output (OUT) and compare (COMP) pins are coupled together. The measurement signal produced by the sensor is available at the connector 694, which is coupled to the signal (SIG) pin of chip 684. The signal produced at the phase error pin represents the difference between the oscillator frequency of chip 684 and the frequency of the measurement signal produced by the sensor.

The phase error pin of chip 684 is also coupled to a circuit that controls LEDs 680 and 682, comprising a transistor 696, a resistor 698, a capacitor 700, two inverters 702 and 704, two NOR gates 706 and 708, two transistors 710 and 712, and two resistors 714 and 716. The difference signal produced at the phase error pin controls transistor 696. When the phase error pulses stop, the circuit turns one of LEDs 680 and 682 on and the other off. More specifically, when the difference signal has a frequency greater than a frequency determined by the time constant defined by resistor 698 and capacitor 700, transistor 696 is essentially maintained in a continuously "on" state. When transistor 696 is on, it turns on transistor 712 via NOR gate 706. Transistor 712 in turn drives LED 682 via resistor 716. When the difference signal has a frequency less than a frequency determined by the time constant defined by resistor 698 and capacitor 700, transistor 696 is essentially maintained in a continuously "off" state. When transistor 696 is off, it turns on transistor 710 via NOR gate 708. Transistor 710 in turn drives LED 680 via resistor 714. Inverters 702 and 704 ensure that one of LED's 680 and 682 is on while the other is off.

A 555-type timer chip 718 causes the LEDs to flash rather than remain on continuously. Its TRIGGER and THRESHOLD pins are coupled together, and a capacitor 720 is coupled between its CONTROL pin and ground. A first resistor 722 is coupled between its DISCHARGE pin and the supply voltage (VCC), and a second resistor 724 is coupled between its DISCHARGE pin and ground via a capacitor 726. The output (OUT) pin of chip 718 is a high frequency clock signal that is coupled via an inverter 727 to the other input of each of NOR gates 706 and 708. Thus, in normal operation, timer chip 718 alternately enables and disables LEDs 680 and 682. Both LEDs 680 and 682 are turned off in response to an error condition, however, because chip 718 is reset and its output pin remains low.

Timer chip 718 is itself disabled or reset when an error condition occurs, thereby causing both of LEDs 680 and 682 to remain off indefinitely. An error circuit is coupled to the RESET pin of chip 718 for this purpose. The error circuit has two R-C circuits, the outputs of which are combined by a NOR gate 728. So long as the measurement signal received from connector 694 is a continuous pulse train, the output of at least one of the R-C circuits is high at any point in time, and the output of NOR gate 728 is high. The output of NOR gate 728 is coupled to the RESET pin of chip 718. An inverter 730 couples the measurement signal to one of the R-C circuits. This R-C circuit comprises a transistor 732, a resistor 734, a capacitor 736 and an inverter 738. The other R-C circuit comprises an inverter 740, a transistor 742, a resistor 744, a capacitor 746 and an inverter 747. If the measurement signal becomes stuck high or low as a result of a sensor malfunction or other error condition, both R-C circuits will simultaneously be in a discharged state, and the output of NOR gate 728 will reset chip 718.

As illustrated in FIGS. 44–52, yet another alternative capacitive sensor 910 includes an elongated, generally rectangular body 912 that is made of a non-conductive material such as plastic the interior of which is coated with a conductive material 913 (see FIG. 52) and thus functions as an outer shield against electric fields. Alternatively, however, body 912 can be made of a conductive material as in embodiments described above. Two endpieces 914 and 916, similarly made of a conductive material or a material having a conductive coating, seal body 912 and thus form part of the shield. As in embodiments described above, sensor 910 has a flow-through configuration that facilitates measurement of a fluid by causing fluid to flow into it through one of endpieces 914 and 916 and out of it through the other. The fluid flows through the measurement chamber, which is defined by the interior of a tube 922 between two plate-shaped or bar-shaped conductors 918 and 920. Tube 922 extends between endpieces 914 and 916 and is made of a non-conductive material. Conductors 918 and 920 are arranged parallel to one another and abutting opposing sides of tube 922. Tube 922 has an oval cross-sectional shape, and conductors 918 and 920 abut the flat sides of the oval. Supports that are integrally formed with body 910 retain tube 922 and conductors 918 and 920.

Figure 53:
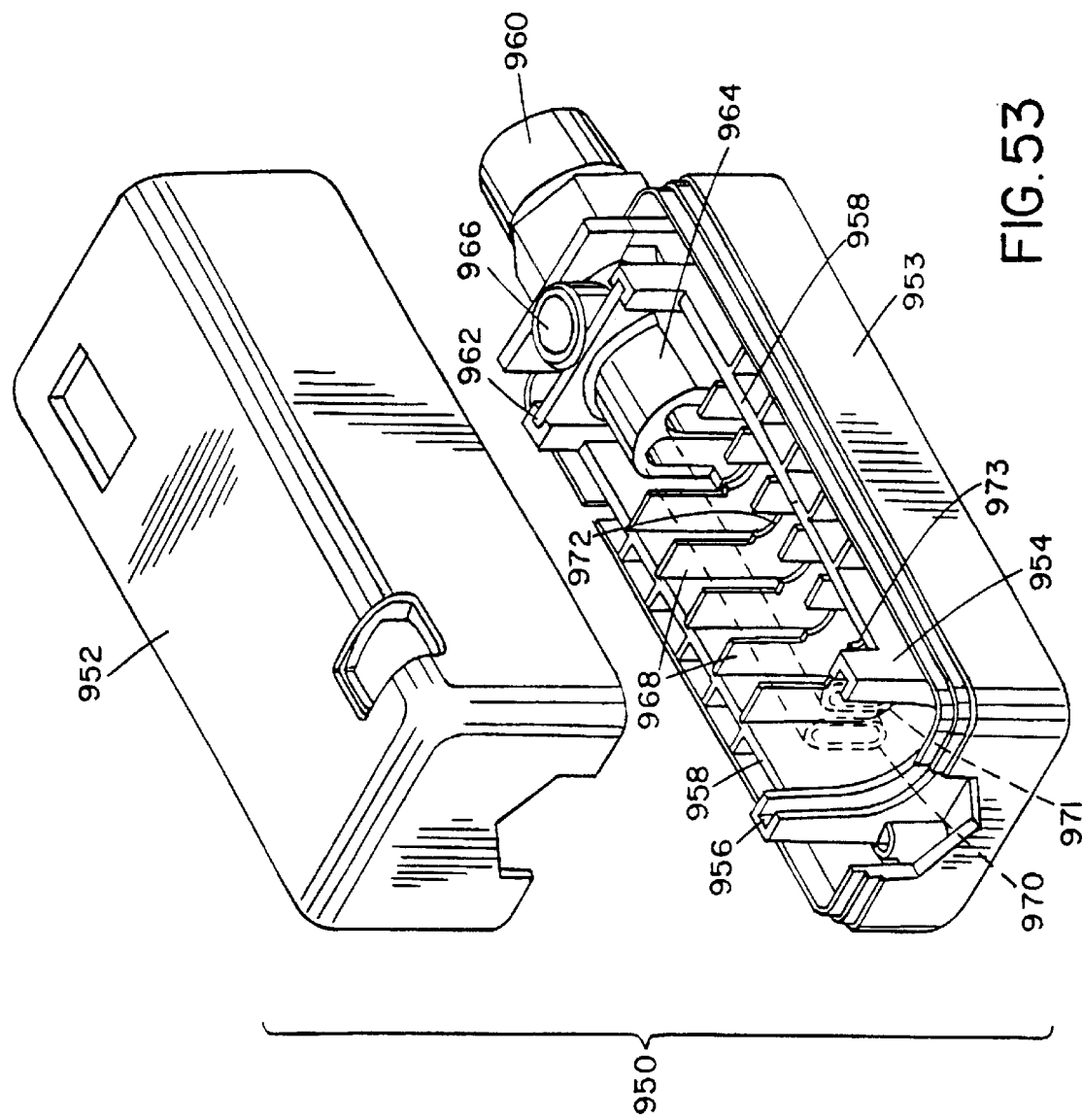
FIG. 53 is a partially exploded perspective view of another alternative embodiment of the sensor.
Figure 54:
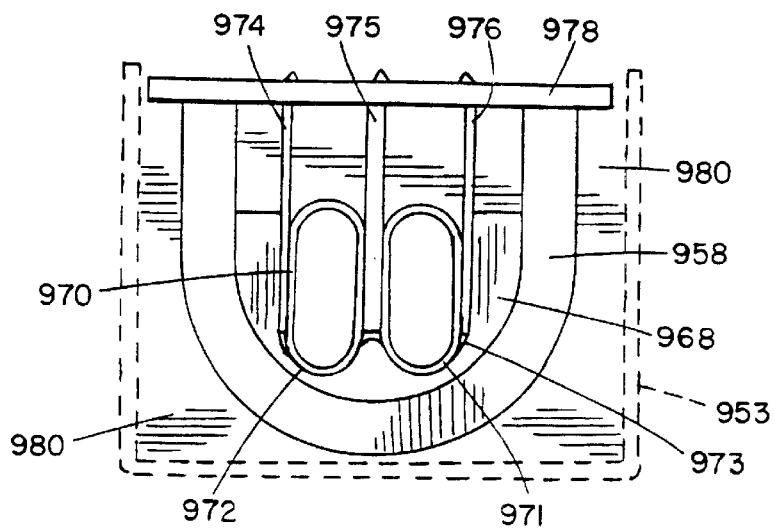
FIG. 54 is an end view of the support structure of the embodiment of FIG. 53.

An alternate embodiment of the sensor of FIGS. 44–52 is illustrated in FIG. 53. Body 950 is configured and constructed in a manner similar to the preceding embodiment. Outer covers 952 and 953 are molded from a non-conductive material and coated on their interior surfaces with a conductive material. The present embodiment differs from the preceding construction in that support structure 954 is formed separately from outer covers 952 and 953, preferably of a molded non-conductive material such as rigid plastic or other polymer. Support structure 954 is dimensioned to be inserted within the outer covers and has longitudinal sidewalls 958 between which a plurality of transverse ribs 968 extend. Each rib 968 has a cut-out to receive one or more tubes through which the material flows. As illustrated in FIGS. 53 and 54, two tubes 970 and 971 (shown in FIG. 53 as dashed lines) are included, and the rib cut-outs are formed to support each tube within its own support area 972 and 973. As shown in FIG. 54, since there are two tubes, three conductor plates 974–976 are provided so that there is a pair of conductors for each tube. Conductor plates 974–976 fit closely within the rib cut-outs so that the plates 974 and 976 are wedged between tubes 970 and 971 and the edges of the rib cut-outs, and plate 975 is wedged into the space between tubes 970 and 971. The separate support area for each tube enhances stability of the tube position and assists in maintaining the conductor plates at a constant separation, by providing mechanical resistance to expansion and contraction which can occur with changes in temperature and/or pressure. Maintaining the relative spacing between the conductors is important for repeatability and reliability of the measurement. Further stabilization of the conductor and tube spacing can be obtained by filling lower cover 953 with an epoxy material 980 after attachment of the tubes 970, 971 and conductor plate 974–976 and PCB 978 assembly. Once set, epoxy 980 provides significantly increased pressure tolerance, so that the sensor can be used under high pressure and/or high flow rate conditions. A sensor so constructed has been tested to 1000 psi without failure. Epoxy 980 can be selected to provide improved thermal insulation, to further isolate the electronics from the effects of environmental variations. An epoxy that has been found to be suitable for purposes of the present invention uses components available from Epoxylite Corporation of Irvine, Calif. This epoxy is a mixture of a resin, sold as Epoxylite #R2, and a catalyst, sold under the name Epoxylite #C321. Selection of other appropriate epoxy components is within the level of skill in the art. The ribs 968 provide additional stabilization by minimizing shrinkage of epoxy 980 as it sets. In an alternate assembly procedure, the epoxy can be injected through a port in the closed housing after all components have been assembled, thus filling the cover 952 and 953 to seal all components to provide stability and improved protection against intrusion of dirt and moisture in harsh environmental conditions.

Figure 55:
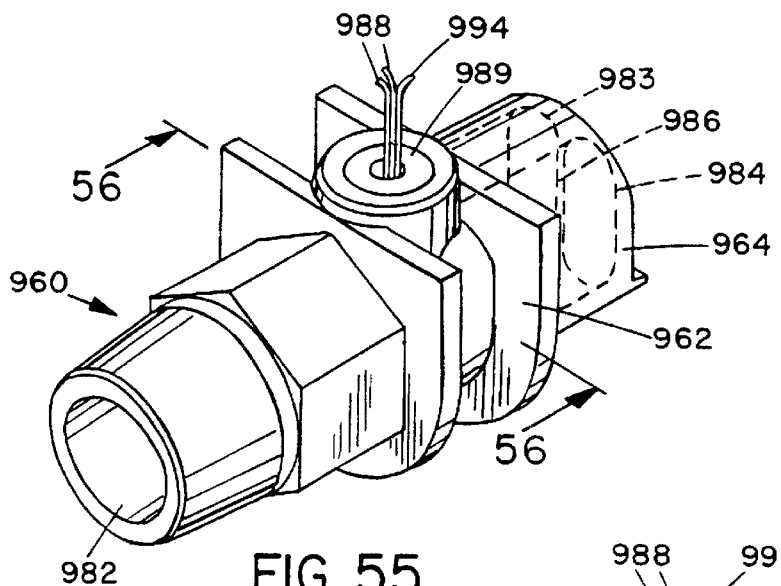
FIG. 55 is a perspective view of an endpiece for use in the embodiment of FIG. 53.
Figure 56:
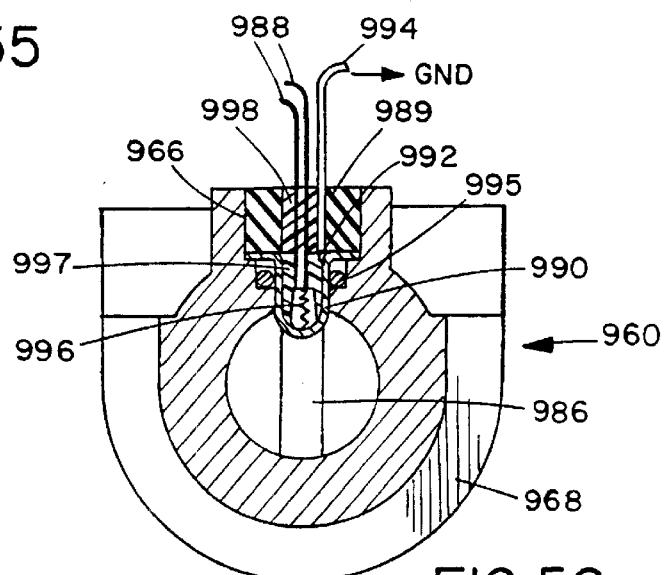
FIG. 56 is a cross-sectional view taken along line 56—56 of FIG. 55.

Support structure 954 also provides for stable attachment of endpieces 960. Note that only one endpiece 960 is shown in FIG. 53 so that support structure 954 can be seen more clearly. Channels 956 are formed in support structure 954 to receive flange 962 of endpiece 960, with flange 962 sliding into channel 956. As shown in FIG. 55, endpiece 960 has a rounded port 982 which is disposed on the exterior side of the sensor which is, in the two tube embodiment, split into two ports 983, 984 within interior portion 964 to which tubes 970 and 971 are attached. Divider 986 is shown in FIG. 56, which is a view from exterior port 982 toward the interior of the sensor.

Bore 966 is formed perpendicular to the axis of endpiece 960 to provide access for electrical connections, including means for discharging static electricity that can be generated by the rapid flow of material through the pipeline. Static electricity can particularly be a problem where the material contains conductive materials, such that the material has a low overall impedance. This static electricity can discharge in the sensors, resulting in spurious signals, inaccurate measurements, and can even damage the sensor's electronics. One or more static discharge conductors, each comprising conductive button 990 or other extension which extends through bore 966 a short distance into the flow channel in endpiece 960, so that it is in electrical contact with the material being measured. In the preferred embodiment, one button 990 is positioned at each endpiece 960 of the sensor, so that static can be discharged both as the material enters and exits the sensor. In the sensor embodiment of FIG. 53, two such buttons will be provided. In sensors having more ports, one discharge button is preferably provided for each port so that, for example, the embodiment of FIG. 29 would have four buttons. Referring to FIG. 56, wire 992 is connected at its first end to button 990 by soldering or other appropriate conductive attachment means as is known in the art. Wire 992 is grounded at its second end 994, typically via a ground connection on the sensor's printed circuit board, allowing the static to be harmlessly discharged. The button material should be inert and non-reactive relative to the material being measured since it will be in direct contact with the material. Appropriate materials can include coatings of metals such as gold, nickel or platinum. In the preferred embodiment, button 990 is stamped brass with a gold coating. An O-ring 995 or other appropriate seal means can be placed or formed around button 990 to create a seal to prevent the escape of material through bore 988. A non-conductive (both thermally and electrically) washer/plug 989 which fits closely within bore 966 is placed on top of button 990 to hold button 990 in place. An open center in plug 989 allows wires to be fed through to be connected to PCB 978.

Temperature-compensation circuitry can be included to minimize drift in measurements arising from environmental and material temperature variations. The actual compensation is performed by the sensor microprocessor or other controller as previously described. As shown in FIG. 56, button 990 is hollow, which allows additional measurement capability to be added in the form of a thermal sensor. Thermistor 996, which is a conventional, commercially available device, is inserted into the hollow interior of button 990, where it can take advantage of the thermal conductivity of the electrically-conductive coating of button 990. Thermistor 996 is sealed in place using a thermally-conductive epoxy 997 or other thermally-conductive material. Above the thermally-conductive epoxy, within the hole in the center of plug 989, between the button and the circuitry to which it attaches to the sensor's circuit board, is a thermally- and electrically- non-conductive epoxy 998 or other seal which prevents the transfer of heat or electricity along any pathway but the thermistor's wires 988. A single thermistor should provide the necessary data and can be included in either the inlet or outlet ports. However, multiple thermistors can be utilized, with one installed at each of any combination of ports, if desired. The described arrangement for installation of a thermistor in a flow-through device is not limited in application to volume charge density measurement devices, but can also be used in other measurement devices for measuring a flowing material.

As in other embodiments described above, sensor 910 includes electronics on a printed circuit board 924 that are also enclosed within the shield defined by body 912 and endpieces 914 and 916. Although not shown for purposes of clarity, sensor 910 may have a suitable indicator, such as a digital display or LED indicator, and may in addition or alternatively, have a cable that provides electrical connections between circuit board 924 and external circuitry, as in other embodiments described above. An electrical connector 926 on circuit board 924 extends through body 912 for this purpose. An important feature of this embodiment is that electrical connection between circuit board 924 and conductors 918 and 920 is made through two tabs 928 and 930 that are integrally formed with conductors 918 and 920, respectively. Tabs 928 and 930 are soldered directly into plated holes in circuit board 924 in the manner of a conventional electronic component. Not only does this arrangement promote manufacturing economy by avoiding additional wires, but it also promotes consistency in the electronic properties among manufactured sensor units. Manufacturing variations in the lengths or positions of wires coupling sensor conductors to sensor electronics can cause measurement variations. The present arrangement overcomes this potential problem by providing tabs 928 and 930 that have a uniform length and are positioned uniformly and securely.

A compensation and calibration method that may be used with the electronic circuits described above is illustrated in FIG. 40. This method is performed prior to beginning measurement. For example, it may be performed at the time of manufacture of the system. Indeed, it may be performed prior to manufacture during an engineering phase in which the system is adapted for a specific use, such as measuring oil as opposed to measuring water. Steps 748, 750, 752 and 754 of the method relate to computing a compensation function to compensate for variation in environmental temperature or for non-linear sensor response. Steps 758, 760, 762 and 764 of the method relate to a two-point calibration method.

At step 748 a material sample of known or predetermined volume charge density is placed in the sensor, which is connected to the circuit in the manner described above with respect to various sensor and circuit embodiments. At step 750, the output of the circuit, which indicates a volume charge density, is recorded along with the known or predetermined volume charge density. At step 752 it is determined whether more data points are to be collected. If more data points are to be collected, another iteration is performed beginning at step 748. In compensating for temperature variation or non-linear sensor response, it is preferred that a multiplicity of such points be collected so as to define a response curve. Parameters other than that for which the compensation function is being computed are held constant. For example, in computing a compensation function for sensor non-linearity, temperature is held constant over all iterations. When all data points have been collected, the function is computed at step 754. A suitable software tool such as MATHCAD may be used to compute the function by fitting a function to the data points. The function, once computed, may be implemented in the circuit using discrete components or may be programmed into a microprocessor, as described above with respect to FIG. 38.

The two-point calibration procedure begins at step 758. At step 758 a material sample of a first known or predetermined volume charge density is placed in the sensor. Preferably, this sample represents the lowest value to be measured, and double-distilled water is a suitable sample for this purpose. At step 760 the circuit is adjusted such that its indicator reads at the lowest end of its scale, e.g., a low-scale indication of zero parts per million (PPM). As described above, this adjustment may be performed, for example, by adjusting the reference oscillators included in some of the exemplary circuits, or by adjusting other suitable components. At step 762 a material sample of a second known or predetermined volume charge density is placed in the sensor. Preferably, this sample represents the highest value to be measured. At step 764 the circuit is adjusted such that its indicator reads at the highest end of the scale, e.g., the predetermined concentration in units of PPM. As described above, this adjustment may be performed by adjusting the gain or delay oscillators included in some of the exemplary circuits, or by adjusting other suitable components.

Figure 41:
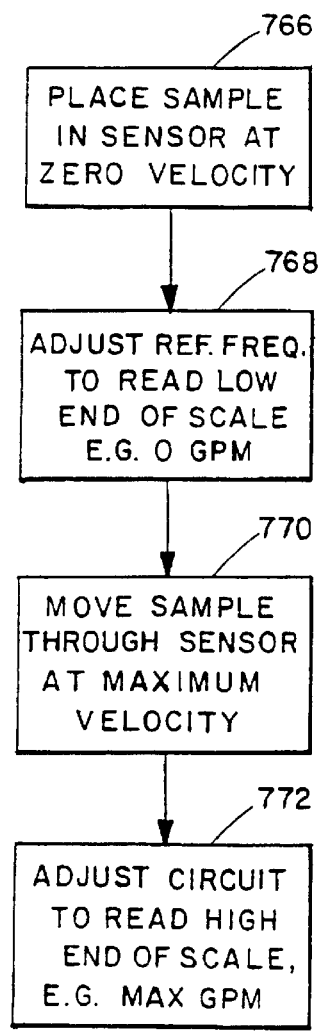
FIG. 41 is a flow diagram illustrating a method for calibrating the system to measure flow velocity.

The system may be used to measure any suitable values, and is not limited to measuring dissolved solids concentrations (in PPM or similar units), as in the examples described above. One novel use for the flow-through embodiments of the sensor is for measuring flow velocity. To measure concentrations, the material sample should have constant velocity with respect to the sensor measurement chamber, because a change in velocity produces a change in the measurement. Thus, to measure flow, the sensor need only be suitably calibrated. An exemplary calibration method is illustrated in FIG. 41. At step 766 a material sample of known or predetermined volume charge density is moved through the sensor at a constant velocity, such as zero. At step 768 the circuit is adjusted such that its indicator reads at the lowest end of its scale, e.g., a low-scale indication of zero gallons per minute (GPM). At step 770 a material sample of known or predetermined volume charge density is moved through the sensor at a second constant velocity. At step 772 the circuit is adjusted such that its indicator reads at the highest end of the scale, e.g., the predetermined flow in units of GPM.

Figure 39:
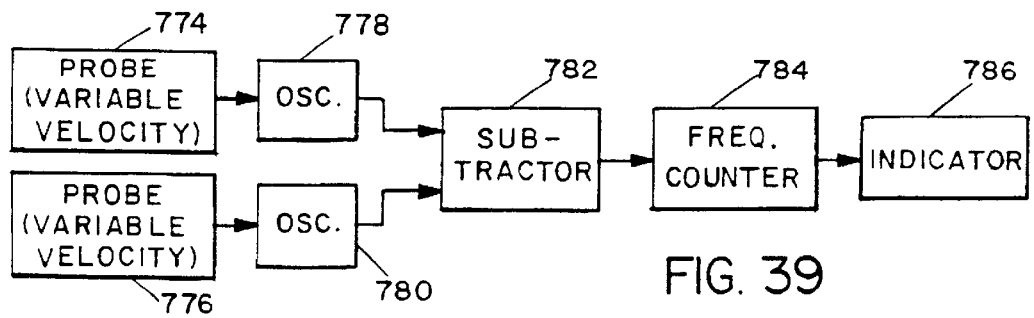
FIG. 39 is a block diagram of still another alternative sensing system that includes two probes or sensors for measuring flow velocity.

As illustrated in FIG. 39, a specialized flowmeter that simplifies calibration may be constructed using the principles of the present invention discussed above. The flowmeter includes two identical probes or sensors 774 and 776, two oscillator circuits 778 and 780, a subtractor circuit 782, a frequency counter circuit 784 and an indicator circuit 786. Sensor 774 receives the fluid at a velocity to be measured. Sensor 776 receives the fluid at a constant velocity. It may, for example, be immersed in the fluid at a zero velocity. Oscillator circuit 778 produces a reference frequency in response to the impedance of sensor 774. Oscillator circuit 780 produces a test frequency in response to the impedance of sensor 776. As in the circuit embodiments described above, subtractor circuit 782 produces a signal representing the difference of these frequencies and thus the measured value. Frequency counter circuit 784 converts this frequency into a digital value and provides it to indicator circuit 786 for display.

Figure 42:
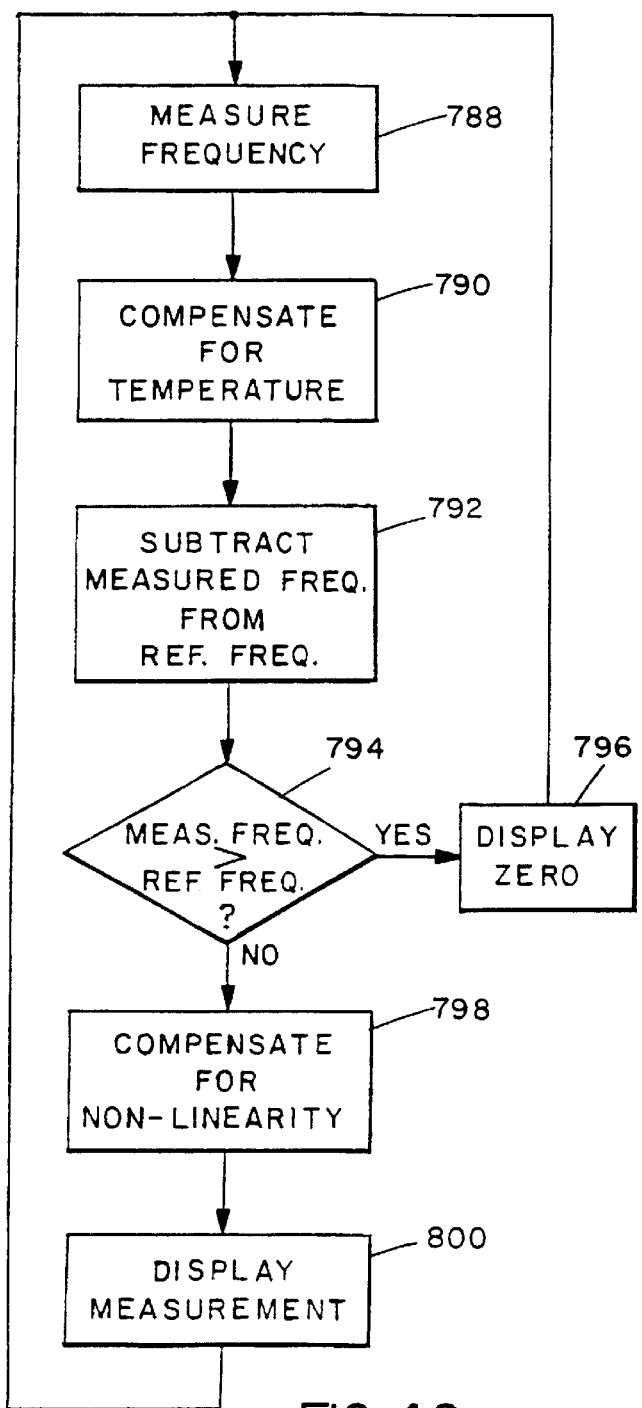
FIG. 42 is a flow diagram illustrating a generalized method of operation of the system.

The measurement process of the system of the present invention can be summarized with reference to FIG. 42. At step 788 the system, comprising the sensor and circuit, measures a frequency in response to the sensor impedance, which reflects the volume charge density (and/or velocity) of the material sample within its measurement chamber. At step 790 the system compensates for environmental temperature by, for example, applying a suitable mathematic function to the measured frequency value. At step 792 the measured or test frequency is subtracted from a reference frequency. Although the term subtraction is used for convenience, any suitable circuit for determining the difference between the test frequency and the reference frequency may be used, ranging from a microprocessor to a differential amplifier to a D-type flip-flop. At step 794 it is determined whether test frequency is greater than the reference frequency. If it is greater, at step 796 a value of zero is provided to the indicator to prevent displaying a negative value. In other words, the displayed value is clamped at zero. If it is not greater, at step 798 the system compensates for non-linear sensor response by, for example, applying a suitable mathematic function to the measured frequency value. At step 800 the difference between the test and reference frequencies is provided to the indicator. The indicator may be a digital display, a binary "go/no-go" display, or any other suitable indicator.

A system incorporating the above-described sensors may be used for a variety of purposes, including measuring the extent of impurities in fluids, such as gases and water and other liquids, and measuring the flow rate of such fluids. Application of such a system can range from, for example, a purified water handling system in an integrated circuit manufacturing facility to desalination plants to oil or gas pipeline monitoring.

Obviously, other embodiments and modifications of the present invention will occur readily to those of ordinary skill in the art in view of these teachings. Therefore, this invention is to be limited only by the following claims, which include all such other embodiments and modifications when viewed in conjunction with the above specification and accompanying drawings.

What is claimed is:

1. A sensor for testing a material sample, comprising:
   a housing having an electrically conductive shield;
   at least one chamber disposed within the housing for containing the material sample, the at least one chamber formed from an electrically non-conductive material and having at least one inlet and at least one outlet for allowing movement of the material sample through the at least one chamber;
   at least two electrical conductors corresponding to and disposed on opposite sides of the at least one chamber;
   a measurement circuit within the housing coupled to the at least two electrical conductors for producing a measurement signal having a frequency responsive to a capacitance defined by the at least two electrical conductors and the material sample between the at least two electrical conductors, the measurement circuit comprising:
      an oscillator circuit coupled to a first electrical conductor of the at least two electrical conductors; and
      a circuit ground potential coupled to a second electrical conductor of the at least two electrical conductors; and
   at least one of a first electrically-conductive extension and a second electrically-conductive extension, wherein
      the first electrically-conductive extension is positioned adjacent the at least one inlet, the first electrically-conductive extension having a first end for contacting the material sample in the at least one chamber, and a second end for connecting to a around potential, the first electrically-conductive extension conducting charges within the material sample to the ground potential; and wherein the second electrically-conductive extension is positioned adjacent the at least one outlet, the second electrically-conductive extension having a first end for contacting the material sample in the at least one chamber, and a second end for connecting to the ground potential, the second electrically-conductive extension conducting the charges within the material sample to the ground potential.

2. The sensor of claim 1, wherein the ground potential, coupled to the first and second electrically-conductive extensions is the circuit around potential.

3. The sensor of claim 1, further comprising a support structure disposed within the housing for supporting the at least one chamber and the at least two electrical conductors, the support structure comprising axial sidewalls with a plurality of rib structures extending therebetween for providing lateral support, each rib structure of the plurality of rib structures having a cut-out portion for receiving the at least one chamber and the at least two electrical conductors.

4. The sensor of claim 3, further comprising an epoxy material filling at least a portion of the housing and the support structure.

5. The sensor of claim 1, further comprising:

an inlet endpiece portion attached to the housing to provide an inlet flow channel into the at least one chamber, the inlet endpiece portion comprising:
an inlet bore formed therethrough to the inlet flow channel;
wherein the first electrically-conductive extension is placed in the inlet bore; and an outlet endpiece portion attached to the housing to provide an outlet flow channel out from the at least one chamber, the outlet endpiece portion comprising:
an outlet bore formed therethrough to the outlet flow channel;
wherein the second electrically-conductive extension is placed in the outlet bore.

6. The sensor of claim 5, wherein the first electrically-conductive extension is a first conductive button disposed within the inlet bore for contacting the material sample, the first conductive button comprising:
an inlet conductor having a first end connected to the first conductive button, and a second end connected to the ground potential, the inlet conductor for conducting the charges within the material sample to the ground potential through the first conductive button; and wherein the second electrically-conductive extension is a second conductive button disposed within the outlet bore for contacting the material sample, the second conductive button comprising
outlet conductor having a first end connected to the second conductive button, and a second end connected to the ground potential, the outlet conductor for conducting the charges within the material sample to the ground potential through the second conductive button.

7. The sensor of claim 6, wherein one of the first conductive button and the second conductive button is a thermally-conductive button having a hollow interior, the thermally-conductive button further comprising:

a thermistor disposed within the hollow interior of the thermally-conductive button, the thermistor having a first end and a second end comprising connecting wires;

a thermally-conducting material disposed within the hollow interior of the thermally-conductive button for retaining the first end of the thermistor therein; and a thermally-insulating material disposed on top of the thermally-conducting material for thermally isolating the first end of the thermistor from the second end;

wherein the second end of the thermistor is connected to the measurement circuit for providing a signal representative of a temperature of the material sample.

8. The sensor of claim 1, wherein the at least one chamber comprises two chambers, and wherein the at least two electrical conductors comprises three conductors comprising an inner conductor disposed between the two chambers and outer conductors disposed outside of the two chambers.

9. The sensor of claim 8, wherein the at least one inlet and the at least one outlet of the two chambers are connected to an inlet endpiece and an outlet endpiece, the inlet endpiece and the outlet endpiece each having an axial bore for allowing movement of the material sample through the two chambers.

10. The sensor of claim 9, wherein the inlet endpiece has an inlet bore formed therethrough for accepting the first electrically-conductive extension, and the outlet endpiece has an outlet bore formed therethrough for accepting the second electrically-conductive extension, wherein each of the first and second electrically-conductive extensions further comprises:

a conductor having a first end connected to the each of the first and second electrically-conductive extensions and a second end connected to the ground potential, the conductor for conducting the charges within the material sample to the ground potential.

11. The sensor of claim 10, wherein at least one of the first and second electrically-conductive extensions is a thermally-conductive extension, the sensor further comprising:

a thermistor disposed within a hollow interior of the thermally-conductive extension, the thermistor having a first end and a second end comprising connecting wires;

a thermally-conducting material disposed within the hollow interior of the thermally-conductive extension for retaining the first end of the thermistor therein; and a thermally-insulating material disposed on top of the thermally-conducting material for thermally isolating the first end of the thermistor from the second end;

wherein the second end of the thermistor is connected to the measurement circuit for providing a signal representative of a temperature of the material sample.

12. The sensor of claim 8, further comprising a support structure disposed within the housing for supporting each of the two chambers and the three conductors, the support structure comprising axial sidewalls with a plurality of rib structures extending therebetween for providing lateral support, each rib structure of the plurality of rib structures having a cut-out portion for receiving the two chambers and the three conductors.

13. The sensor of claim 12, further comprising an epoxy material filling at least a portion of the housing and the support structure.

14. A sensor for measuring a volume charge density of a fluid, the sensor comprising:

a conductive housing for providing a shield against outside electric fields;

at least one chamber inside of the conductive housing and held by a support structure, the at least one chamber formed from an electrically non-conductive material and providing a flow channel for the fluid;

at least two conductive plates placed on opposite sides of the at least one chamber and held by the support structure;

a measurement circuit coupled to the at least two conductive plates for producing a measurement signal having a frequency responsive to a capacitance defined by the at least two conductive plates and the fluid contained in the flow channel of the at least one chamber, the measurement circuit comprising:
excitation circuitry coupled to a first conductive plate of the at least two conductive plates; and
a circuit ground coupled to a second conductive plate of the at least two conductive plates;

an inlet end piece connected to a first end of the at least one chamber for receiving the fluid into the flow channel;

an outlet end piece connected to a second end of the at least one chamber for discharging the fluid from the flow channel; and at least one electrically-conductive extension connected to one of the inlet end piece and the outlet end piece, the at least one electrically-conductive extension having a first end for contacting the fluid in the at least one chamber, and a second end for connecting to a ground potential, the at least one electrically-conductive extension conducting a charge within the fluid to the around potential.

15. The sensor of claim 14,
wherein at least one of the inlet end piece and the outlet end piece comprises: a bore extending therethrough to the flow channel; and
wherein the at least one electrically-conductive extension is an electrically-conductive button for placement in the bore, the electrically-conductive button having a first end for contacting the fluid in the flow channel, and a second end for connection to the ground potential, the electrically-conductive button conducting the charge within the fluid to the ground potential.

16. The sensor of claim 15, wherein the electrically-conductive button is a thermally-conductive button having a hollow interior, the sensor further comprising:
a thermistor disposed within the hollow interior of the thermally-conductive button, the thermistor coupled to the measurement circuit for providing a signal representative of a temperature of the fluid;
a thermally-conducting material disposed within the hollow interior of the thermally-conductive button for retaining the thermistor therein; and
a thermally-insulating material disposed within said bore on top of the thermally-conducting material for thermally isolating the thermistor from the measurement circuit.

17. The sensor of claim 14 wherein each of the inlet end piece and the outlet end piece have an interior surface in contact with the fluid in the flow channel and an exterior surface, and wherein at least one of the inlet end piece and the outlet end piece comprises:
a bore extending from the exterior surface to the interior surface; and
wherein the at least one electrically conductive extension is an electrically-conductive button for placement in the bore, the electrically-conductive button having a first end for contacting the fluid in the flow channel of the at least one chamber, and a second end for connection to the ground potential, the electrically-conductive button conducting the charge within the fluid to the ground potential.

18. The sensor of claim 17, wherein the electrically-conductive button of at least one of the inlet end piece and the outlet end piece has a hollow interior, the sensor further comprising:
a thermistor disposed within the hollow interior of the electrically-conductive button, the thermistor coupled to the measurement circuit for providing a signal representative of a temperature of the fluid.

19. A sensor for testing a fluid, the sensor comprising:
a conductive housing for providing a shield against outside electric fields;
at least one chamber inside of the conductive housing and held by a support structure, the at least one chamber formed from an electrically non-conductive material and providing a flow channel for the fluid;
at least two conductive plates placed on opposite sides of the at least one chamber and held by the support structure;
a measurement circuit coupled to the at least two conductive plates for producing a measurement signal having a frequency responsive to a capacitance defined by the at least two conductive plates and the fluid contained in the flow channel of the at least one chamber;
an inlet end piece connected to a first end of the at least one chamber for receiving the fluid into the flow channel, and an outlet end piece connected to a second end of the at least one chamber for discharging the fluid from the flow channel, each of the inlet end piece and the outlet end piece comprising:
an exterior surface;
an interior surface in contact with the fluid in the flow channel;
a bore extending from the exterior surface to the interior surface; and
an electrically-conductive button for placement in the bore, the electrically-conductive button having a first end for contacting the fluid in the flow channel, and a second end for connection to a ground potential, the electrically-conductive button conducting a charge within the fluid to the ground potential; and
a thermistor disposed within a hollow interior of the electrically-conductive button of at least one of the inlet end piece and the outlet end piece, the thermistor having a lower end adjacent the first end of the electrically conductive button and an upper end comprising connecting wires, wherein the upper end of the thermistor is connected to the measurement circuit for providing a signal representative of a temperature of the fluid.

20. The sensor of claim 19, wherein the at least one chamber comprises a first chamber and a second chamber, and wherein the at least two conductive plates comprises an inner conductor plate disposed between the first, chamber and the second chamber, and a first outer conductor plate and second outer conductor, plate disposed outside of the first chamber and the second chamber, the inner conductor plate and the first outer conductor plate providing a pair of conductors for the first chamber, and the inner conductor plate and the second outer conductor plate providing a pair of conductors for the second chamber.

* * * * *